United States Patent [19]

Brown et al.

[11] Patent Number: 4,898,863

[45] Date of Patent: Feb. 6, 1990

[54] HETEROCYCLIC CARBOXAMIDES

[75] Inventors: Frederick J. Brown, Newark, Del.; Ying K. Yee, Kennett Square, Pa.

[73] Assignee: ICI Americas Inc., Wilmington, Del.

[21] Appl. No.: 38,842

[22] Filed: Apr. 15, 1987

[30] Foreign Application Priority Data

Apr. 15, 1986 [GB] United Kingdom ................. 8609175

[51] Int. Cl.$^4$ ................. A61K 31/535; A61K 31/405; C07D 211/06; C07D 209/14

[52] U.S. Cl. ................. 514/235.2; 514/255; 514/323; 514/445; 514/419; 544/132; 544/143; 544/371; 544/373; 546/201; 546/199; 548/253; 548/494; 548/503

[58] Field of Search ..................... 514/415, 419, 235.2, 514/255, 323; 548/505, 253, 494; 544/132, 143, 371, 373; 546/201, 199

[56] References Cited

U.S. PATENT DOCUMENTS 3,271,416 9/1966 Shen et al. .
3,415,841 12/1968 Nordmann et al. .
3,470,298 9/1969 Palazzo .
4,277,489 7/1981 Vandoni .
4,499,299 2/1985 Bernstein et al. .

FOREIGN PATENT DOCUMENTS 234103 6/1964 Austria .
671445 4/1966 Belgium .
54417 6/1982 European Pat. Off. .
107618 5/1984 European Pat. Off. .
166591 1/1986 European Pat. Off. .
179619 4/1986 European Pat. Off. .
2854987 6/1980 Fed. Rep. of Germany .
7631 1/1970 France .

OTHER PUBLICATIONS

Hannig, e., et al., *Pharmazie* (1974), 29, H. 10-11, 685-686.
Marx, J. L., *Science* (1982), 215, 1380-1382.
Krell, R. D., *J. Pharmacol. Exp. Ther.* (1979), 211, 436-433.
Fleisch, J. H, et al., *J. Pharmacol Exp. Ther.* (1985), 233, 148-157.
Cook, J. A., et al., *J. Pharmacol. Exp. Ther.* (1985), 235, 470-474.
Denzlinger, C., et al., *Science* (1985), 230, 330-332.

*Primary Examiner*—Joseph Paul Brust
*Assistant Examiner*—Mary Sue Howard
*Attorney, Agent, or Firm*—Rosemary M. Miano; Thomas E. Jackson

[57] ABSTRACT

This invention provides a series of novel heterocyclic carboxamides of formula I in which the group $-Y-Z<$ is selected from $-C(Ra)=C<$, $-N=C<$, and $-CH(Ra)-CH<$ and the other radicals have the meanings defined in the following specification.

The compounds of formula I are leukotriene antagonists. The invention also provides pharmaceutically acceptable salts of the formula I compounds; pharmaceutical compositions containing the formula I compound, or their salts, for use in the treatment of, for example, allergic or inflammatory diseasxes, or endotoxic or traumatic shock conditions; and processes for the manufacture of the formula I compounds, as well as intermediates for use in such manufacture.

14 Claims, No Drawings

HETEROCYCLIC CARBOXAMIDES

SUMMARY AND BACKGROUND OF THE INVENTION

This invention concerns novel heterocyclic carboxamide derivatives and, more particularly, novel benzoic acids (and related tetrazoles and acylsulphonamides), derived from indolecarboxamides, indazolecarboxamides and indolinecarboxamides which antagonise the pharmacological actions of one or more of the arachidonic acid metabolites known as leukotrienes (hereinafter referred to as "leukotriene antagonist properties"). The novel derivatives are useful whenever such antagonism is desired. Thus, such compounds may be of value in the treatment of those diseases in which leukotrienes are implicated, for example in the treatment of allergic disorders, such as, for example, asthma, or of inflammatory diseases, or of endotoxic or traumatic shock conditions. The invention also provides pharmaceutical compositions containing the novel derivatives for use in such treatments, and processes and intermediates for the manufacture of the novel derivatives.

In European Patent Application publication No. 0 107 618 A1 are disclosed N-substituted-2-(1-imidazoylyl)-indoles which possess thromboxane synthetase inhibitor properties. We have now discovered a series of indole, indazole and indoline derivatives which have a carboxamidic substituent in the benzenoid ring and a particularly substituted alkyl group in the 3-position and which unexpectedly possess the property of antagonising one or more of the arachidonic acid metabolites known as leukotrienes and this is the basis for our invention.

DESCRIPTION OF THE INVENTION

According to the invention there is provided a compound of formula I (Formula set out on pages following Examples)  I wherein the group —Y—Z< is selected from a group consisting of:
  (a) —C(Ra)=C<
  (b) —N=C<
  (c) —CH(Ra)—CH<
in which "<" indicates two separate bonds;
Ra is hydrogen or (1–4C)alkyl;
Rb is hydrogen or methyl;
$R^1$ is (2–10C)alkyl optionally containing 1 or more fluorine substituents; or $R^1$ is phenyl-(1–6C)alkyl in which the (1–6C)alkyl moiety may optionally bear a fluoro or (1–4C)alkoxy substituent and in which the phenyl moiety may optionally bear a substituent selected from a group consisting of halogeno, (1–4C)alkyl, (1–4C)alkoxy and trifluoromethyl; or $R^1$ is (3–8C)cycloalkyl or (3–8C)cycloalkyl-(1–6-C)alkyl, the cyclic moiety of any of which optionally may contain one unsaturated linkage and may optionally bear 1 or 2 (1–4C)alkyl substituents;
L is a (1–10C)alkylene link, optionally containing one double or triple bond;
P is a polar group selected from a group consisting of cyano, 1H-tetrazol-5-yl, carbamoyl of formula $CONR^2R^3$, ureido of formula $NR^4CONR^2R^3$, carbamoyloxy of formula $OCONR^2R^3$, a carbamate of formula $NR^4COOR^5$, acylamino of formula $NR^4COR^5$, acyloxy of a formula $OCOR^5$, and an (optionally oxidized) thio group of formula $S(O)_nR^5$ in which
$R^2$ is selected from a group consisting of hydrogen, (1–6C)alkyl, and phenyl, the phenyl moiety of which may optionally bear 1 or 2 substituents selected from a group consisting of halogeno, (1–4C)alkyl, (1–4C)alkoxy and trifluoromethyl, and
$R^3$ and $R^4$ are independently selected from a group consisting of hydrogen and (1–6C)alkyl;
or $R^2$ and $R^3$ together with the adjacent nitrogen form a pyrrole, pyrrolidine, piperidine, morpholine, piperazine or N-(1–6C)alkylpiperazine ring, and $R^4$ is hydrogen or (1–6C)alkyl:
$R^5$ is chosen from a group consisting of (1–4C)alkyl and phenyl, the phenyl moiety of which may optionally bear 1 or 2 substituents selected from a group consisting of halogeno, (1–4C)alkyl, (1–4C)alkoxy and trifluoromethyl; and
n is the integer 0, 1 or 2;
Rc is selected from a group consisting of hydrogen and (1–4C)alkoxy; and
M is an acidic group selected from a group consisting of carboxy, an acylsulphonamide residue of formula —$CO.NH.SO_2R^6$ and 1H-tetrazol-5-yl in which
$R^6$ is selected from a group consisting of (1–6C)alkyl, (3–8C)cycloalkyl, (6–12C)aryl, heteroaryl comprising 5–12 atoms at least one of which is carbon and at least one of which is selected from oxygen, sulfur, and nitrogen, and (6–12C)aryl-(1–4C)alkyl, in which any of the aromatic or heteroaromatic moieties may bear 1 or 2 substituents selected from a group consisting of halogeno, (1–4C)alkyl, (1–4C)alkoxy, and trifluoromethyl;
or a pharmaceutically acceptable salt thereof.

It will be appreciated that certain of the compounds of formula I, for example those wherein $R^1$ contains an asymmetrically substituted carbon atom, may exist in, and be isolated in, optically-active and racemic forms. In addition, it will be appreciated that certain compounds of formula I, for example, those wherein L contains a double bond, may exist in, and be isolated in, separate stereoisomeric forms ('E' and 'Z') about that group. Some compounds may exist in more than one tautomeric form. Some compounds may exhibit polymorphism. It is to be understood that the present invention encompasses any racemic, optically-active, tautomeric, polymorphic or stereoisomeric form, or mixtures thereof, which form possesses leukotriene antagonist properties, it being well known in the art how to prepare optically-active forms (for example, by resolution of the racemic form or by synthesis from optically-active starting materials) and individual 'E' and 'Z' stereoisomers (for example, by chromatographic separation of a mixture thereof) and how to determine the leukotriene antagonist properties by the standard tests described hereinafter.

In this specification L, P, M, $R^1$, Ra, et cetera stand for generic radicals and have no other significance. It is to be understood that the generic term "(1–6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, "alkylene" and "alkenylene" et cetera. Halogeno is fluoro, chloro, bromo or iodo.

Included in the ranges and values for the generic radicals are those wherein:

Ra is hydrogen;

Rb is hydrogen or methyl;

$R^1$ is (3–7C)alkyl optionally containing 1 or more fluorine substituents: or $R^1$ is phenyl-(1–4C)alkyl in which the (1–4C)alkyl moiety may optionally bear a fluoro or (1–4C)alkoxy substituent and in which the phenyl moiety may optionally bear a substituent selected from a group consisting of halogeno, (1–4C)alkyl, (1–4C)alkoxy and trifluoromethyl; or $R^1$ is (3–6C)cycloalkyl or (3–6C)cycloalkyl-(1–4C)alkyl, the cyclic moiety of any of which optionally may contain one unsaturated linkage and may optionally bear 1 or 2 (1–4C)alkyl substituents;

L is a (1–5C)alkylene link, optionally containing one double or triple bond;

P is a polar group selected from a group consisting of cyano, 1H-tetrazol-5-yl, carbamoyl of formula $CONR^2R^3$, carbamoyloxy of formula $OCONR^2R^3$, and an (optionally oxidized) thio group of formula $S(O)_nR^5$ in which $R^2$ is selected from a group consisting of hydrogen, (1–6C)alkyl, and phenyl, the phenyl moiety of which may optionally bear 1 or 2 substituents selected from a group consisting of halogeno, (1–4C)alkyl, (1–4C)alkoxy and trifluoromethyl, and $R^3$ is hydrogen or (1–6C)alkyl;

or $R^2$ and $R^3$ together with the adjacent nitrogen form a pyrrole, pyrrolidine, piperidine, morpholine, piperazine or N-(1–6C)alkylpiperazine ring;

$R^5$ is chosen from a group consisting of (1–4C)alkyl and phenyl, the phenyl moiety of which may optionally bear 1 or 2 substituents selected from a group consisting of halogeno, (1–4C)alkyl, (1–4C)alkoxy and trifluoromethyl; and n is the integer 1 or 2;

Rc is selected from a group consisting of hydrogen and (1–4C)alkoxy; and

M is an acidic group selected from a group consisting of carboxy, an acylsulphonamide residue of formula $-CO.NH.SO_2R^6$ and 1H-tetrazol-5-yl in which $R^6$ is selected from a group consisting of (1–4C)alkyl, (3–6C)cycloalkyl, (6–12C)aryl, heteroaryl comprising 5–12 atoms at least one of which is carbon and at least one of which is selected from oxygen, sulfur, and nitrogen, and (6–12C)aryl-(1–4C)alkyl, in which any of the aromatic or heteroaromatic moieties may bear 1 or 2 substituents selected from a group consisting of halogeno, (1–4C)alkyl, (1–4C)alkoxy, and trifluoromethyl.

Particular values for the ranges of generic radicals described above under L, P, M, $R^1$, Ra et cetera are as follows:

A particular value for $R^1$ when it is (2–10C)alkyl is, for example, ethyl, propyl, isopropyl, butyl, isobutyl, sec-butyl, t-butyl, pentyl, 3-methylbutyl, 1-ethylpropyl, hexyl, heptyl, 1-ethylpentyl or nonyl: and when it contains 1 or more fluorine substituents a particular value is, for example, 2,2,2-trifluoroethyl.

Particular values for $R^1$ when it is phenyl(1–6C)alkyl include, for example, benzyl, 1-phenylethyl, 2-phenylethyl, 1-phenylpropyl, 2-phenylpropyl, 3-phenylpropyl, 1-methyl-1-phenylethyl, 1-phenylbutyl and 1-phenylpentyl; and a particular value for an optional (1–4C)alkoxy substituent on the (1–6C)alkyl moiety is, for example, methoxy or ethoxy.

Particular values for certain optional substituents which may be present on a phenyl moiety of $R^1$, or as a part thereof, as defined above include, for example:

for halogeno: a member selected from a group consisting of fluoro, chloro and bromo;

for (1–4C)alkyl: a member selected from a group consisting of methyl and ethyl; and for (1–4C)alkoxy: a member selected from a group consisting of methoxy and ethoxy.

A particular value for $R^1$ when it is (3–8C)cycloalkyl is, for example, cyclopropyl, cyclobutyl, cyclopentyl, cyclohexyl or cycloheptyl; when $R^1$ is (3–8C)cycloalkyl-(1–6C)alkyl a particular value is, for example, cyclobutylmethyl, cyclopentylmethyl, cyclohexylmethyl, 1-cyclopentylethyl, 2-cyclopentylethyl, 1-cyclopentylpropyl, 1-cyclohexylpropyl, 1-cyclopentylbutyl, 1-cyclohexylbutyl; and a particular value for $R^1$ when it is a radical containing an unsaturated linkage in the cycloalkyl ring is, for example, cyclopentenyl, cyclohexenyl, cyclopentenyl(1–6C)alkyl (such as cyclopentenylmethyl) or cyclohexenyl-(1–6C)alkyl (such as 1-cyclohexen-4-ylmethyl or 1-(cyclohexenyl)butyl); and a particular value for an optional (1–4C)alkyl substituent on the cyclic moiety of such a radical is, for example, methyl, ethyl or isopropyl.

A particular value for L when it is (1–10C)alkylene is, for example, methylene, ethylene, ethylidene, trimethylene, tetramethylene, 1,1-dimethylethylene, 2,2-dimethylethylene, pentamethylene, or hexamethylene. When L contains one double bond, a particular value is, for example, vinylene, 1-propenylene, 2-propenylene, 2-methylvinylene, 1-butenylene, 2-butenylene, 1,2-dimethylvinylene, 1,1-dimethyl-2-propenylene or 3,3-dimethyl-1-propenylene, and when it contains one triple bond is, for example, ethynylene, 1-propynylene, 2-propynylene, 2-butynylene, 1,1-dimethyl-2-propynylene or 3,3-dimethyl-1-propynylene;

A particular value for $R^2$, $R^3$, $R^4$, or the N-substituent of a piperazine when it is (1–6C)alkyl is, for example, methyl, ethyl, propyl, isopropyl, butyl, t-butyl or pentyl;

A particular value for $R^5$ or Ra when it is (1–4C)alkyl is, for example, methyl, ethyl, propyl or isopropyl;

Particular values for optional substituents which may be present on a phenyl moiety of $R^2$ or $R^5$ include those defined above in connection with a phenyl moiety in $R^1$.

A particular value for Rc when it is (1–4C)alkoxy is, for example, methoxy or ethoxy;

A particular value for $R^6$ when it is (1–6C)alkyl is, for example, methyl, ethyl, propyl, isopropyl or butyl; when $R^6$ is (3–8C)cycloalkyl a particular value is, for example, cyclopentyl or cyclohexyl; when $R^6$ is (6–12C)aryl a particular value is, for example, phenyl, 1-naphthyl or 2-naphthyl; when $R^6$ is heteroaryl a particular value is, for example, furyl, thienyl or pyridyl; and when $R^6$ is (6–12C)aryl-(1–4C)alkyl a particular value is, for example, benzyl, 1-naphthylmethyl or 2-naphthylmethyl.

Particular values for optional substituents which may be present on an aromatic or heteroaromatic moiety of $R^6$ include those defined above in connection with a phenyl moiety in $R^1$.

Thus, particular values for the radicals include for $R^1$: cyclopentylmethyl; for Ra and Rb: hydrogen; for Rc: methoxy; for L: methylene, ethylene, 2-methylethylene, and vinylene; for M: carboxy and an acylsulphonamide residue of formula —CO.NH.SO$_2$R$^6$ in which R$^6$ is phenyl or 2-methylphenyl; and for P: cyano, carbamoyl of formula CONR$^2$R$^3$ and carbamoyloxy of formula OCONR$^2$R$^3$ wherein R$^2$ and R$^3$ are independently hydrogen or methyl, or R$^2$ and R$^3$ together with the adjacent nitrogen form a pyrrolidine or morpholine ring.

More particular values for the groups listed above include by way of example those selected from the groups consisting of:

for R$^1$: ethyl, propyl, isopropyl, butyl, isobutyl, sec-butyl, t-butyl, pentyl, 3-methylbutyl, 1-ethylpropyl, hexyl, heptyl, 1-ethylpentyl, nonyl, benzyl, 4-chlorobenzyl, 4-trifluoromethylbenzyl, 4-methylbenzyl, 1-phenylethyl, 2-phenylethyl, 1-methyl-1-phenylethyl, 1-phenylpropyl, 1-phenylpentyl, cyclopentyl, cyclohexyl, cyclobutylmethyl, cyclopentylmethyl, cyclohexylmethyl, 2-cyclopentylethyl, 1-cyclopentylbutyl, 1-cyclohexylpropyl, 1-cyclohexylbutyl, cyclopentenylmethyl, and 1-cyclohexen-4-ylmethyl;

for R$^2$: hydrogen, methyl, ethyl, propyl, isopropyl, t-butyl, phenyl, 2-methylphenyl and 4-chlorophenyl;

for R$^3$ and R$^4$ (independently selected): hydrogen, methyl and ethyl;

for R$^2$ and R$^3$ together with the adjacent nitrogen: piperidine, morpholine, and N-methylpiperazine;

for R$^5$: methyl, ethyl, propyl, isopropyl, phenyl, 2-methylphenyl and 4-chlorophenyl;

for R$^6$: methyl, isopropyl, butyl, cyclopentyl, phenyl, 4-chlorophenyl, 4-methylphenyl, 2-chlorophenyl, 2-methylphenyl, 2-methoxyphenyl, naphthyl, thien-2-yl and 6-chloropyrid-3-yl;

for Ra: hydrogen and methyl;

for Rb: hydrogen; and for Rc: hydrogen and methoxy.

Examples of specific groups which are of special interest include those selected from groups consisting of:

for R$^1$: butyl, 3-methylbutyl, 1-ethylpentyl, 1-phenylpropyl, cyclopentyl, and cyclopentylmethyl;

for R$^6$: phenyl, 2-methylphenyl;

for Ra: hydrogen; and for Rc: methoxy.

It will be appreciated that within the above definitions there are included a number of sub-groups of compounds, for example:

(i) indoles of formula Ia;

(Formula set out on pages following Examples)    Ia (ii) indazoles of formula Ib;

(Formula set out on pages following Examples)    Ib and (iii) indolines of formula Ic;

(Formula set out on pages following Examples)    Ic together with the pharmaceutically acceptable salts thereof.

In the above sub-groups a preferred value for M is a radical of formula —CO.NH.SO$_2$R$^6$ wherein R$^6$ is phenyl, optionally substituted as defined above, for example, 2-methylphenyl. A preferred value for R$^1$ is (3–6C)cycloalkyl-(1–4C)alkyl and, especially, cyclopentylmethyl.

Preferred groups of compounds of the invention comprise the indole derivatives of formula IIa:

(Formula set out on pages following Examples)    IIa and indazole derivatives of formula IIb:

(Formula set out on pages following Examples)    IIb wherein R$^1$, L, M and P have any of the meanings defined above, together with the pharmaceutically acceptable salts thereof.

Specific compounds of the invention are described in the accompanying examples. However, of these the compounds N-[4-[6-(N-cyclopentylmethylcarbamoyl)-3-[2-(morpholinocarbonyl)ethyl]indol-1-ylmethyl]-3-methoxybenzoyl]-2-methylbenzenesulphonamide and N-[4-[6-(N-cyclopentylmethylcarbamoyl)-3-[2-(pyrrolidinocarbonyl)ethyl]indol-1-ylmethyl]-3-methoxybenzoyl]-2-methylbenzenesulphonamide are particularly preferred and may be used either in the free acid form or as their corresponding pharmaceutically acceptable salts.

Examples of suitable pharmaceutically acceptable salts are salts formed with bases which form a physiologically acceptable cation, such as alkali metal (especially sodium and potassium), alkaline earth metal (especially calcium and magnesium), aluminum and ammonium salts, as well as salts made with appropriate organic bases such as triethylamine, morpholine, piperidine and triethanolamine. For those compounds of formula I which are sufficiently basic, examples of suitable pharmaceutically acceptable salts include acid-addition salts such as those made with a strong acid, for example hydrochloric, sulphuric or phosphoric acid.

The compounds of formula I may be made by processes which include processes known in the chemical art for the production of structurally analogous heterocyclic compounds. Such processes for the manufacture of a compound of formula I as defined above are provided as further features of the invention and are illustrated by the following procedures in which the meanings of generic radicals are as defined above, T is defined as a radical selected from a group consisting of COORh (wherein Rh has the values defined below), CN, and the values defined above for M; U is defined as a suitable leaving group, for example, halogeno (especially chloro, bromo, or iodo) or alkane- or arene-sulphonyloxy (especially methanesulphonyloxy or p-toluenesulphonyloxy); and Hal is defined as chloro, bromo or iodo:

(A) For a compound of formula I wherein M is a carboxy group, decomposing a suitable ester of formula III:

(Formula set out on pages following Examples)    III wherein Rh is a conveniently removed acid protecting group, for example, phenyl, benzyl, or (1–6C)alkyl optionally bearing an acetoxy, (1–4C)alkoxy or (1–4C)alkylthio substituent.

A particular value for Rh is, for example, methyl, ethyl, propyl, t-butyl, acetoxymethyl, methoxymethyl, 2-methoxyethyl, methylthiomethyl, phenyl, or benzyl.

Certain of the starting esters of formula III may be active in their own right as leukotriene antagonists (such as, for example, by in vivo conversion to the corresponding carboxylic acid), for example, those wherein Rh is (1-6C)alkyl, and they are included within the scope of the invention.

It will be appreciated that the decomposition can be performed using any one of a variety of procedures well known in the art of organic chemistry. Thus, it may be carried out, for example, by conventional hydrolysis under acid or base conditions, adjusted as necessary to minimize any hydrolytic removal of other functional groups in the molecule. Also, when Rh is methyl, the ester may be decomposed by nucleophilic demethylation with, for example, lithium thioethoxide in a solvent such as N,N'-dimethylpropyleneurea. Alternatively, it may in certain circumstances, for example, when Rh is t-butyl, be possible to carry out the decomposition by thermal means, for example, by heating the ester of formula III at a temperature of, for example, 100°–150° C., alone or in a suitable solvent or diluent such as diphenylether. In addition, when Rh is t-butyl the decomposition may be performed, for example, by using trimethylsilyl triflate and then water, in a conventional manner. Still further, in certain circumstances, for example, when Rh is benzyl, it may be possible to carry out the decomposition by reductive means, for example, by the use of hydrogen at about atmospheric pressure in the presence of a suitable catalyst, such as palladium or platinum, conveniently on charcoal as a support.

A preferred method for decomposing an ester of formula III comprises reacting the ester with a suitable base, for example, an alkali or alkaline earth metal hydroxide or carbonate (such as lithium hydroxide, potassium hydroxide, sodium hydroxide, calcium hydroxide or potassium carbonate) in a suitable aqueous solvent or diluent, for example, water, optionally together with a water-miscible alkanol, glycol, ketone or ether (such as methanol, ethanol, ethylene glycol, 2-methoxyethanol, acetone, methyl ethyl ketone, tetrahydrofuran or 1,2-dimethoxyethane), at a temperature of, for example, 15°–100° C. and conveniently at or near ambient temperature. When such a method is employed, the resulting carboxylic acid of formula I, wherein M is a carboxy group, is initially obtained as the corresponding salt of the base used for the hydrolysis and may be isolated as such or converted to the free acid form by a conventional acidification procedure, for example, by reaction with a suitable strong acid such as hydrochloric or sulphuric acid.

(B) Acylating an amine of formula R¹NHRb with a carboxylic acid (or a reactive derivative thereof) of formula IV:

(Formula set out on pages following Examples)   IV but wherein T is chosen from the values defined for M. When M is a carboxy group, a preferred reactive derivative of the carboxy group shown in formula IV is a lower alkyl ester of the carboxy group shown in formula IV, for example, the methyl ester.

When an acid halide derivative of a compound of formula IV is used as the acylating agent, a suitable base such as triethylamine, N-methylmorpholine, pyridine, 2,6-lutidine or 4-(dimethylamino)pyridine is conveniently also employed, preferably together with a suitable inert solvent or diluent, for example, dichloromethane, diethyl ether, tetrahydrofuran or 1,2-dimethoxyethane.

Alternatively, a suitable condensing agent, for example, a carbodiimide (such as dicyclohexylcarbodiimide or 1-(3-dimethylaminopropyl)-3-ethylcarbodiimide, or a salt thereof) or 1,1'-carbonyldiimidazole, may be employed with an acid of formula IV, preferably together with a suitable inert solvent or diluent, for example, one of those mentioned above for use with an acid halide.

When a lower alkyl ester derivative of a compound of formula IV is used as an acylating agent, the reaction is preferably performed in the absence of any condensing agent or diluent and in the presence of an excess of the amine R¹NHRb.

In general, the acylations are carried out at a temperature in the range of, for example, −20° to 60° C. and, conveniently, at or near ambient temperature.

(C) For a compound of formula I wherein —Y—Z< has the value (a) defined hereinabove, reacting an indole of formula V:

(Formula set out on pages following Examples)   V but wherein T is chosen from the values defined for M, with a reagent of formula U.L.P, in the presence of a suitable Lewis acid.

A particularly suitable Lewis acid is, for example, silver oxide, silver carbonate, silver fluoroborate, silver trifluoroacetate, silver trifluoromethanesulfonate, zinc chloride, ferric chloride or stannic chloride.

In general, the process is performed in a suitable solvent or diluent, for example, in acetone, dichloromethane, acetonitrile or an ether solvent such as 1,2-dimethoxyethane, dioxane or tetrahydrofuran, optionally together with a hydrocarbon diluent such as toluene or xylene, and at a temperature in the range of, for example, 15°–100° C. and, more preferably, in the range of 40°–80° C.

Alternatively, in the absence of a Lewis acid catalyst, the process is generally performed in a suitable solvent or diluent, for example, in a polar solvent (such as N,N-dimethylformamide, N,N'-dimethylpropyleneurea or N-methylpyrrolidone) or in an ether solvent (such as dioxane or 1,2-dimethoxyethane), optionally together with a hydrocarbon diluent such as toluene or xylene; and the alkylation is generally performed at a temperature in the range of, for example 50°–160° C., and, preferably, in the range of 70°–100° C.

(D) Reacting an amino compound of formula VI:

(Formula set out on pages following Examples)   VI with an alkylating agent of formula VII:

(Formula set out on pages following Examples)   VII but wherein T is chosen from the values defined for M.

The reaction is preferably performed in the presence of a suitable base, for example, an alkali metal hydride such as sodium or potassium hydride in a suitable inert solvent or diluent, for example, tetrahydrofuran, 1,2-dimethoxyethane, N-methylpyrrolidone, or N,N-dimethylformamide. Alternatively, the compound of formula VI may be used in the form of its preformed anhydrous alkali metal salt, for example, by prior reaction with a suitable base such as sodium or potassium methoxide, t-butoxide or hydride, or butyl lithium; in which case a wider range of conventional solvents or diluents may be employed for the reaction with the alkylating agent.

In either case, the alkylation is generally performed at a temperature in the range of, for example, −10° to 40° C. and, conveniently, at or near ambient temperature.

(E) For a compound of formula I wherein M is a 1H-tetrazol-5-yl radical, reacting a cyano derivative of formula VIII:

(Formula set out on pages following examples) VIII with an azide.

A particularly suitable azide is, for example, an alkali metal azide such as sodium or potassium azide, preferably together with an ammonium halide, for example, ammonium chloride or ammonium bromide or, especially, with triethylammonium chloride. The reaction is preferably performed in a suitable polar solvent, for example, N,N-dimethylformamide or N-methylpyrrolidone, and conveniently at a temperature in the range of, for example, 50° to 160° C.

(F) For a compound of formula I wherein M is a group of formula $CO.NH.SO_2.R^6$, reacting a compound of formula I wherein M is carboxy (which compound is hereinafter referred to as "acid of formula I") with a sulphonamide derivative of formula $R^6.SO_2.NH_2$ in the presence of a dehydrating agent or reacting a reactive derivative of an acid of formula I with a sulphonamide, or a salt thereof, of formula $R^6.SO_2.NH_2$.

Thus, for example, a free acid of formula I may be reacted with a suitable dehydrating agent, for example, with dicyclohexylcarbodiimide or 1-(3-dimethylaminopropyl)-3-ethylcarbodiimide, or with a hydrochloride or hydrobromide salt thereof, optionally together with an organic base, for example, 4-(dimethylamino)pyridine, and with a sulfonamide of formula $R^6.SO_2.NH_2$ in the presence of a suitable solvent or diluent, for example, dichloromethane, at a temperature in the range of, for example, 10° to 50° C., but preferably at or near ambient temperature.

Alternatively, a reactive derivative of an acid of formula I, for example, an acid halide (such as the acid chloride), acid anhydride or a mixed acid anhydride (such as that formed from N,N-diphenylcarbamic acid and the acid of formula I by reaction of the sodium salt of the latter acid with N,N-diphenylcarbamoylpyridinium chloride), may be reacted with an alkali metal salt (such as the lithium, sodium or potassium salt) of the appropriate sulphonamide of formula $R^6.SO_2.NH_2$, conveniently at or near ambient temperature and in a suitable solvent or diluent, for example, tetrahydrofuran, N,N-dimethylformamide or dichloromethane.

(G) For a compound of formula I wherein —Y—Z> has the value (c) defined above, catalytic hydrogenation of an indole of formula I wherein —Y—Z> has the value (a) defined above.

Particularly suitable catalytic hydrogenation conditions are those of catalytic transfer hydrogenation, for example, palladium-on-carbon (10% w/w) and formic acid (99%) at a temperature in the range of, for example, 15°-100° C., more preferably in the range of 70°-85° C.

(H) Reduction of the double bond of a compound of formula I in which L contains one double bond to provide the corresponding compound of formula I in which L contains no double bond.

Preferred reduction conditions include, for example, catalytic hydrogenation over palladium on carbon in a suitable solvent such as methanol, ethanol or tetrahydrofuran at ambient temperature, and, optionally, the addition of an equivalent of a base, such as, for example, potassium hydroxide or triethyl amine.

(I) For a compound of formula I in which P is a carbamoyl group of the formula $CONR^2R^3$, acylation of an amine of the formula $HNR^2R^3$ with a corresponding acid (or a reactive derivative thereof, including suitable esters) of formula IX:

(Formula set out on pages following Examples) IX but wherein T is chosen from the values defined for M.

When M is a carboxy group, it is preferred to use a lower alkyl ester derivative of the carboxy group shown in formula IX as the reactive derivative, for example, the methyl ester. The reaction may be performed using similar procedures to those described above in part (B).

(J) For a compound of formula I in which P is a 1H-tetrazol-5-yl group, reacting a nitrile of formula X:

(Formula set out on pages following Examples) X but wherein T is chosen from the values defined for M, with an azide using similar procedures to those described above in part (E).

(K) For a compound of formula I in which P has the value $NR^4CONR^2R^3$, $OCONR^2R^3$, $NR^4COOR^5$, $NR^4COR^5$ or $OCOR^5$, acylating a compound of formula XI:

(Formula set out on pages following Examples) XI but wherein T is chosen from the values defined for M and wherein QH has the value $NR^4H$ or OH, with an appropriate acylating agent, for example, an isocyanate of the formula $R^2NCO$, a carbamoyl halide of formula $Hal.CONR^2R^3$, a haloformate of formula $Hal.COOR^5$, a mixed carbonate such as $(4\text{-nitrophenoxy}).COOR^5$, an acid halide such as $Hal.COR^5$ or a mixed anhydride such as $O(COR^5)_2$.

In general, the process is performed at a temperature in the range of, for example, 0°-60° C. and conveniently in a suitable inert diluent or solvent such as methylene chloride, diethyl ether, tetrahydrofuran or dioxane. When an acid halide is used as the acylating agent, a suitable base such as triethylamine, N-methylmorpholine, piperidine or 4-(dimethylamino)pyridine is conveniently also employed.

(L) For a compound of formula I in which P has the value $S(O)_nR^5$ and n is 0, reacting a compound of formula XII:

(Formula set out on pages following Examples) XII but wherein T is chosen from the values defined for M, with a mercaptan of formula $R^5SH$.

In general, the process is performed using an appropriate base, such as, for example, potassium carbonate, sodium hydroxide or sodium hydride, at a temperature in the range of, for example, 0° to 80° C., and, optionally, in a suitable inert diluent or solvent such as, for example, acetone, tetrahydrofuran, dioxane, or N,N-dimethylformamide.

(M) For a compound of formula I in which P has the value $S(O)_nR^5$ and n is 1 or 2, oxidizing the corresponding compound I in which n is 0 or n is 1.

In general, the process is performed at a temperature in the range of, for example, −20° to 60° C. in a suitable inert diluent or solvent such as, for example, methylene chloride, tetrahydrofuran or diethyl ether or aqueous methanol and with a suitable oxidant such as, for example, potassium peroxymonosulfate, sodium periodate or a peroxy acid such as, for example, m-chloroperbenzoic acid.

(N) For a compound of formula I wherein L contains a double bond adjacent to Z, reacting an aldehyde or ketone of formula XIII:

(Formula set out on pages following Examples)   XIII but wherein T is chosen from the values defined for M and wherein $R^7$ is selected from hydrogen and (1–4C)alkyl, with an appropriate zwitterionic or carbanionic reagent, such as, for example, that derived from a phosphonium salt or a phosphonate by treatment with a base.

The reaction is preferably performed with an excess of a zwitterionic reagent, such as, for example, cyanomethylenetriphenylphosphorane, or of a carbanionic reagent in a suitable inert solvent or diluent such as, for example, tetrahydrofuran, dioxane, 1,2-dimethoxyethane, N,N-dimethylformamide or dimethylsulfoxide at a temperature in the range of, for example, 20° to 100° C.

It may be desired to optionally use a protecting group during all or portions of the above described processes (A)–(N); the protecting group then may be removed when the final compound is to be formed.

In general, when a compound of formula I wherein M is a carboxylic acid is required, it is preferred to carry out one of the procedures (B), (C), (D), (G), (H), (K), (M) and (N) mentioned above using an appropriate carboxylic ester and liberating the required acid as a final step using procedure (A) above.

Pharmaceutically acceptable salts may be obtained using standard procedures well known in the art, for example, by reacting a compound of formula I with a suitable base affording a physiologically acceptable cation or by reacting a sufficiently basic compound of formula I with a suitable acid affording a physiologically acceptable anion.

If not commercially available, the necessary starting materials for the above procedures may be made by procedures which are selected from standard techniques of heterocyclic chemistry, techniques which are analogous to the synthesis of known, structurally similar compounds, and techniques which are analogous to the above described procedures or the procedures described in the examples.

Thus, for example, for those intermediates in which —Y—Z< has the value (a) (—C(Ra)=C<), which are indoles, preparation may begin with the corresponding 2-substituted indole-6-carboxylic acid which may be converted to a corresponding amide of formula XIV:

(Formula set out on pages following Examples)   XIV using a similar procedure to one of process (B). Substitution of an intermediate of formula XIV, at the N(1)- and C(3)-position may be carried out in a series of steps in any convenient order.

By using a similar procedure to that described in process (D) and using a compound of formula VII, a compound of formula XIV, wherein —Y—Z< has the value (a), may be converted into a corresponding indole of formula V. An indole of formula V may serve as an intermediate for outer starting materials in which the value of —Y—Z< is (a). For example, using a similar method to method (C), a compound of formula V, but wherein T has the value COORh, may be converted into a compound of formula III, wherein —Y—Z< has the value (a). Similarly, a compound of formula V, but wherein T has the value CN, may be converted into a compound of formula VIII wherein —Y—Z< has the value (a). Also, by using a similar procedure to that of the process (C) and an appropriate alkylating agent (or protected version thereof, followed by deprotection), an indole of formula V may be converted into a corresponding intermediate of formula IX, X, XI, or XII, wherein —Y—Z< has the value (a).

Alternatively, an indole of formula XIV may be first alkylated at the C(3)-position using a similar procedure to that described in process (C) to afford a corresponding compound of formula VI wherein —Y—Z< has the value (a). By using a similar process to process (C) and an appropriate alkylating agent (or a protected version thereof, followed by deprotection) and then using a similar process to process (D) and an appropriate compound of formula VII as an alkylating agent, an indole of formula XIV may be converted into a corresponding intermediate of formula III, VIII, IX, X, XI or XII, wherein —Y—Z< has the value (a).

In addition a compound of formula XIV may be acylated at the C(3)-position with, for example, the appropriate N,N-dimethylamide of formula $(CH_3)_2NCOR^7$ and phosphorous oxychloride and subsequently alkylated at the N(1)-position with a compound of formula VII employing a similar procedure to those described in part (D) to afford a compound of formula XIII, but wherein —Y—Z< has the value (a).

In general, an indoline intermediate in which —Y—Z< has the value (c) (—CH(Ra)—CH<) may be obtained by using a similar procedure to process (G) and from a corresponding indole in which —Y—Z< has the value (a).

Starting materials in which —Y—Z< has the value (b) (—N=C<) conveniently may be prepared from indazole-6-carboxylic acid, which may be (i) brominated to provide 3-bromoindazole-6-carboxylic acid, (ii) converted into an amide by using a similar procedure to that described in process (B), and (iii) alkylated at the N(1)-position using a similar procedure to that of process (D) and a compound of formula VII as an alkylating agent to provide an indazole of formula XV:

(Formulas set for on pages following Examples)   XV in which T' has the value COORh or CN.

An indazole of formula XV, but wherein T' has the value COORh, may be converted into a starting material of formula III wherein —Y—Z< has the value (b) by a cross coupling reaction using a transition metal catalyst such as, for example, dichloro[1,1'-bis(diphenylphosphino)ferrocene]palladium(II) and a reagent such as, for example, Br.Zn.L.P, provided that the moiety -L.P does not interfere with the reaction or undergo reaction under the conditions, and an appropriate solvent or diluent such as, for example, ether or tetrahydrofuran at a temperature in the range of, for example, 0° to 25° C. If the moiety -L.P does interfere with the reaction or undergo reaction under the conditions, a protected form may be used, followed by deprotection.

Similarly, a starting material of formula VIII wherein —Y—Z< has the value (b) may be obtained from a compound of formula XV, but wherein T' has the value CN, and a reagent such as, for example, Br.Zn.L.P, or a protected derivative thereof.

By using analogous methodology and a compound of formula XV, a starting material of formula IX, X, XI or XII, but wherein —Y—Z< has the value (b), and wherein T has the value COORh or CN, may be obtained from a corresponding precursor to the C(3) substituent, or a protected or latent form, thereof, followed by deprotection or elaboration.

When a starting material of formula IV is desired, instead of converting a starting indole-6-carboxylic acid or indazole-6-carboxylic acid into an amide by a similar process to process (B), (i) the acid may be converted into its corresponding ester, for example, of an alcohol of a formula RhOH; (ii) processes analogous to those described above may be carried out, and (iii) the ester may be decomposed to afford the acid IV using a similar procedure to one of those described for process (A).

In general, an intermediate compound having the value Rb as methyl may be obtained from a corresponding compound having the value Rb as hydrogen by alkylation using, for example, a base such as sodium hydride, a methylating agent such as iodomethane or dimethylsulfate, and a solvent such as N,N-dimethylformamide at a temperature in the range of 0°–25° C.

Also, intermediates of formula XIII may be converted into other corresponding intermediates of formulae III, VIII, IX, X, XI and XII by standard methods of organic chemistry.

Generally, starting esters of formula III or starting nitriles of formula VIII, respectively, may be made using general procedures similar to those described in (D) by using VII, wherein T has the value COORh or CN, respectively, as an alkylating agent. Also, generally, starting esters of formula III or starting nitriles of formula VIII, may be made using similar general procedures to those described in (B) and (C) using corresponding intermediates IV and V but wherein T stands for COORh or CN, as appropriate, in said intermediates.

A nitrile of formula VIII may be obtained from a corresponding compound of formula I wherein M is carboxy by treatment with, for example, chlorosulphonyl isocyanate and N,N-dimethylformamide. Alternatively, a cyano compound of formula VIII may be obtained by conventional dehydration of the primary amide derived from a corresponding carboxylic acid of formula I wherein M is carboxy.

The intermediate alcohols and amines of formula XI, wherein —Y—Z< has the value (a), may be obtained by alkylation of the corresponding compounds of formula V with reagents of the formula U.L.QH (in which QH is optionally protected) using similar procedures to those described in part (C) above.

Alternatively, the intermediate alcohols of formula XI wherein Q is oxygen may be obtained by selective reduction of the corresponding acids of formula IX using, for example, diborane in tetrahydrofuran at ambient temperature.

The intermediates XII may be obtained from the corresponding alcohols XI wherein Q is oxygen by appropriate transformations, for example, by reaction with p-toluenesulphonyl chloride, with methanesulphonyl chloride, or with triphenylphosphine and carbon tetrachloride or carbon tetrabromide in an appropriate solvent.

The majority of the starting materials of formulae III, IV, V, VI, VIII, IX, X, XI and XII are novel and are provided as further features of the invention based on their utility as chemical intermediates.

As stated previously, the compounds of formula I possess leukotriene antagonist properties. Thus, they antagonise at least one of the actions of one or more of the arachidonic acid metabolites known as leukotrienes, for example, $C_4$, $D_4$, and/or $E_4$, which are known to be powerful spasmogens (particularly in the lung), to increase vascular permeability and which have been implicated in the pathogenesis of asthma and inflammation (see J. L. Marx, *Science*. 1982, 215, 1380–1383) as well as of endotoxic shock (see J. A. Cook, et al., *J. Pharmacol. Exp. Ther.*, 1985, 235, 470) and traumatic shock (see C. Denzlinger, et al., *Science*, 1985, 230, 330). Thus, the compounds of formula I may be useful in the treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic eczema, psoriasis, as well as vasospastic cardiovascular disease, and endotoxic and traumatic shock conditions.

The compounds of formula I are potent leukotriene antagonists and are useful whenever such activity is desired. For example, the compounds of formula I are of value as pharmacological standards for the development and standardization of new disease models and assays for use in developing new therapeutic agents for treating the diseases in which the leukotrienes are implicated.

When used in the treatment of one or more of the above mentioned diseases, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; in the form of aerosols or nebuliser solutions or suspensions for administration by inhalation; and in the form of powders together with pharmaceutically acceptable inert solid diluents such as lactose for administration by insufflation.

For oral administration a tablet or capsule containing up to 250 mg (and typically 5 to 100 mg) of a compound of formula I may conveniently be used. Similarly, for intravenous or intramuscular injection or infusion a sterile solution or suspension containing up to 10% w/w (and typically 0.05 to 5% w/w) of a compound of formula I may conveniently be used.

The dose of compound of formula I to be administered will necessarily be varied according to principles well known in the art taking account of the route of administration and the severity of the condition and the size and age of the patient under treatment. However, in general, a compound of formula I will be administered to a warm-blooded animal (such as man) so that a dose in the range of, for example, 0.05 to 25 mg/kg (and usually 0.5 to 10 mg/kg) is received.

The leukotriene antagonist properties of a compound of formula I may be demonstrated using standard tests. Thus, for example, they may be demonstrated in vitro using the standard guinea-pig tracheal strip preparation described by Krell (*J. Pharmacol. Exp. Ther.*, 1979, 211, 436). Using this procedure, tracheal tissue strips are set up in groups of eight, four being used as time/vehicle (dimethyl sulfoxide) controls and four for each test compound. All of the strips are exposed to $8 \times 10^{-9}$M leukotriene E$_4$(LTE$_4$) following the 50 minute equilibration period, and the response is recorded. This $8 \times 10^{-9}$M concentration of LTE$_4$ is that which produces a contraction equal to about 70-80% of the maximal effect of the agonist in this tissue. The LTE$_4$ is washed out for 40-45 minutes and the procedure is repeated twice to ensure that reproducible responses are being obtained with LTE$_4$. Leukotriene C$_4$(LTC$_4$) or D$_4$(LTD$_4$), at a concentration of $8 \times 10^{-9}$M, may be substituted for LTE$_4$ in the same procedure.

Once tissue reproducibility has been established, test compounds are added to four baths following the 40-45 minute washout period. After a 10 minute incubation with test compound or vehicle, $8 \times 10^{-9}$M LTE$_4$, LTD$_4$ or LTC$_4$ is added and the response recorded. The percentage inhibition by the test compound or the percentage change in vehicle controls is calculated, for each tissue, according to the following equation: % inhibition=100 multiplied by (mg tension increase of preceding response minus mg tension increase in presence of compound) divided by mg tension increase of preceding response. The mean percentage change for vehicle controls and test compound are calculated and evaluated for significant differences by Student's t-test for unpaired data. Tissues exposed to test compounds are retested for responsiveness to LTE$_4$, LTD$_4$ or LTC$_4$ following a 45 minute washout period. If tissue responsiveness is equal to responsiveness preceding exposure to the test compound additional studies are conducted. If responsiveness is not restored by the washing procedure, the tissues are discarded. The cyclooxygenase inhibitor, indomethacin, is present at $5 \times 10^{-6}$M in all the determinations.

In general, the compounds of formula I tested demonstrated statistically significant activity as LTC$_4$, LTD$_4$ and/or LTE$_4$ antagonists in the above test at a concentration of about $10^{-5}$M or much less.

The selectivity of action of these compounds as leukotriene antagonists as opposed to non-specific smooth muscle depressants may be shown by carrying out the above in vitro procedure using the non-specific spasmogen barium chloride at a concentration of $1.5 \times 10^{-3}$M, again in the presence of indomethacin at $5 \times 10^{-6}$M.

Activity as a leukotriene antagonist may also be demonstrated in vivo in laboratory animals, for example, in a routine guinea-pig aerosol test in which guinea-pigs are pre-dosed with test compound (generally between 15 minutes to 1 hour) before an aerosol challenge of leukotriene LTD$_4$ (starting with 3 ml of a 30 microgram/ml solution) and the effect of the test compound on the average time of leukotriene initiated change in breathing pattern (such as onset of dyspnoea) recorded and compared with that in undosed, control guinea-pigs. In general, compounds of formula I tested produced a significant increase in the time of onset of leukotriene initiated breathing changes following either oral or intravenous administration or by inhalation at a dose of about 100 mg/kg, or much less, without any indication of untoward side-effects at several multiples of the minimum effective dose, for example, the compound of Example 8 is effective following oral administration at a dose of 2 mmole/kg and shows no sign of overt toxicity following oral administration at a dose of 30 mmole/kg.

The invention will now be illustrated by the following non-limiting examples in which, unless stated otherwise:

(i) temperatures are given in degrees Celsius (C.): operations were carried out at room or ambient temperature, that is, at a temperature in the range of 18°-25°;

(ii) evaporation of solvent was carried out using a rotary evaporator under reduced pressure (600-4000 pascals; 4.5-30 mm Hg) with a bath temperature of up to 60°;

(iii) flash chromatography was carried out on Merck Kieselgel (Art 9385) and column chromatography on Merck Kieselgel 60 (Art 7734); [these materials were obtained from E. Merck, Darmstadt, W. Germany]: thin layer chromatography (TLC) was carried out on Analtech 0.25 mm silica gel GHLF plates (Art 21521), obtainable from Analtech, Newark, Del., U.S.A:

(iv) in general, the course of reactions was followed by TLC and reaction times are given for illustration only;

(v) melting points are uncorrected and (d) indicates decomposition: the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) when given, NMR data is in the form of delta values for major diagnostic protons, given in parts per million (ppm) relative to tetramethylsilane (TMS) as an internal standard, determined at 80 MHz or 250 MHz using CDCl$_3$, DMSO-d$_6$ or CD$_3$OD as solvent; conventional abbreviations for signal shape are used, for example: s, singlet; d, doublet; m, multiplet; br, broad: etc.; in addition "Ar" signifies an aromatic group or signal;

(ix) reduced pressures are given as absolute pressures in pascals (Pa); other pressures are given as gauge pressures in bars;

(x) chemical symbols have their usual meanings; the following abbreviations have also been used: v (volume), w (weight); mp (melting point), l [liter(s)], ml (milliliters), g [gram(s)], mg [milligram(s)]; an (xi) solvent ratios are given in volume: volume (v/v) terms.

EXAMPLE 1

4-[6-(N-Cyclopentylmethylcarbamoyl)-3-[2-(N-methylcarbamoyl)ethyl]indol-1-ylmethyl]-3-methoxybenzoic acid A mixture of 4-[6-(N-cyclopentylmethylcarbamoyl)-3-(2-methoxycarbonylethyl)indol-1-ylmethyl]3-methoxybenzoic acid (0.3 g) and 4-(dimethylamino)-pyridine (0.07 g) was combined with condensed methylamine (75 ml) in a pressure vessel. The mixture was stirred for 24 hours. The amine was then allowed to evaporate. The residue was dissolved in water and acidified with 10% (v/v) hydrochloric acid. The resultant precipitate was collected by filtration and washed with water to give the title compound (0.26 g, 89%) as a white powder; mp 274°–275°.

Analysis calculated for: $C_{28}H_{33}N_3O_5 \cdot 0.1\ H_2O$: C, 68.13; H, 7.15; N, 8.51 Found: C, 67.83: H, 6.75: N, 8.46.

The starting material was prepared as follows:

(a) A solution of methyl 4-methyl-3-nitrobenzoate (4.46 g) in N,N-dimethylformamide (23 ml) was treated with N,N-dimethylformamide dimethyl acetal (8.18 g) and heated at 130° C. for 2 hours. The solvent was evaporated and the residue was triturated with ether to give methyl E-4-(2-dimethylaminovinyl)3-nitrobenzoate (5.58 g, 98%) as a red powder; NMR (80 MHz, $CDCl_3$) 2.98[s, 6H, $N(CH_3)_2$], 5.90(d, 1H, CHN), 7.14(d, 1H, CHCHN), 7.45(d, 1H, $H^5$-Ar), 7.90(dd, 1H, $H^6$-Ar), 8.47(d, 1H, $H^2$-Ar).

(b) A solution of methyl E-4-(2-dimethylaminovinyl)-3-nitrobenzoate (5.58 g) in tetrahydrofuran (100 ml) was hydrogenated at 3.45 bar in the presence of 10% (w/w) palladium on carbon (1.1 g) for 35 minutes. The catalyst was removed by filtration through diatomaceous earth and the filtrate was evaporated. The residue was dissolved in ethyl acetate and the solution obtained was washed successively with 10% (v/v) hydrochloric acid, water, and brine, then dried ($MgSO_4$) and evaporated to give methyl indole-6-carboxylate (3.32 g, 85%) as a white solid; NMR (80 MHz, $CDCl_3$) 3.92(s, 3H, $OCH_3$), 6.57(m, 1H, $H^3$-indole), 7.32(t, 1H, $H^2$-indole), 7.10(d, 1H, $H^4$-indole), 7.87(dd, 1H, $H^5$-indole), 8.16(broad s, 1H, $H^7$-indole).

(c) A solution of methyl indole-6-carboxylate (11.0 g) in a mixture of tetrahydrofuran (150 ml), methanol (150 ml), and water (63 ml) was treated with lithium hydroxide monohydrate (15.8 g). The mixture was stirred at 60° C. for 6 hours and then concentrated to remove the organic solvents. The residue was dissolved in water, and the solution was acidified with 50% (v/v) hydrochloric acid. The precipitate which formed was collected by filtration and dried to give indole-6-carboxylic acid (9.6 g, 95%) as a tan powder; mp 253°–254°: NMR (80 MHz; $CDCl_3$) 6.51(m, 1H, $H^3$-indole), 8.04(m, 1H, $H^7$-indole), 11.43(broad s, 1H, NH), 12.42(broad s, 1H, OH).

(d) A solution of indole-6-carboxylic acid (9.41 g) and 1,1′carbonyldiimidazole (10.6 g) in methylene chloride (290 ml) was heated at reflux, under nitrogen, for 30 minutes. The solution was cooled and treated with cyclopentylmethylamine (7.0 g). This mixture was heated to reflux for 30 minutes. The resultant solution was then diluted with methylene chloride, washed successively with 10% (v/v) hydrochloric acid, 20% (w/v) aqueous sodium hydroxide, and brine, dried ($MgSO_4$), and evaporated to give 6-(N-cyclopentylmethylcarbamoyl)indole (14.4 g, 91%) as an ivory powder, mp 148°–150°; NMR (80 MHz, DMSO-$d_6$): 3.19(dd, 2H, $CH_2NH$), 6.46(br d, 1H, $H^3$-indole), 7.91(d, 1H, $H^7$-indole), 8.29(t, 1H, $CH_2NH$).

(e) N,N-Dimethylformamide (DMF)(20 ml) was cooled to 0° under an atmosphere of nitrogen and treated cautiously with phosphorus oxychloride (6.6 ml). This solution was stirred at 0° for 15 minutes, warmed to room temperature, and treated with a solution of 6-(N-cyclopentylmethylcarbamoyl)indole (14.3 g) in DMF (100 ml). The yellow mixture was stirred for 2 hours and then brought to pH 14 by the addition of ice and 20% (w/v) aqueous sodium hydroxide. The mixture was heated to reflux for 5 minutes and allowed to cool. The precipitate which formed was collected by filtration and triturated with ether to give 6-(N-cyclopentylmethylcarbamoyl)-3-formylindole (9.6 g, 60%) as a tan powder; mp 224°–225°.

(f) A mixture of 6-(N-cyclopentylmethylcarbamoyl)-3-formylindole (0.92 g), t-butyl 4-bromomethyl-3-methoxybenzoate (1.2 g), and potassium carbonate (0.7 g) in N,N-dimethylformamide (17 ml) was stirred for 48 hours under a nitrogen atmosphere. Water was added to give a precipitate which was collected by filtration and dried to yield t-butyl 4-[6-(N-cyclopentylmethylcarbamoyl)-3-formylindol-1-ylmethyl]-3-methoxybenzoate (1.2 g, 71%) as an ivory powder; mp 134°–135°.

(g) A solution of t-butyl 4-[6-(N-cyclopentylmethylcarbamoyl)-3-formylindol-1-ylmethyl]-3-methoxybenzoate (1.2 g) and methyl (triphenylphosphoranylidene)acetate (1.8 g) in dioxane (12 ml) was heated at reflux for 48 hours. The solvent was evaporated. The resultant residue was purified by flash chromatography on silica gel (600 ml), eluting with 3:7 ethyl acetate:hexane, to give t-butyl 4-[6-(N-cyclopentylmethylcarbamoyl)-3-(2-methoxycarbonylvinyl)indol-1-ylmethyl]-3-methoxybenzoate (1.1 g, 84%) as a yellow solid; mp 163°–164°.

(h) A solution of t-butyl 4-[6-(N-cyclopentylmethylcarbamoyl)-3-(2-methoxycarbonylvinyl)indol-1-ylmethyl]-3-methoxybenzoate (1.11 g) in methanol (10 ml) was treated with 10% (w/w) palladium on carbon (0.28 g) and shaken under 3.45 bars of hydrogen for 24 hours. The catalyst was removed by filtration through diatomaceous earth, and the filtrate was evaporated to give t-butyl 4-[6-(N-cyclopentylmethylcarbamoyl)-3-(2-methoxycarbonylethyl)indol-1-ylmethyl]-3-methoxybenzoate (1.04 g, 94%) as a grey foam, mp 58°–60°.

(i) A solution of t-butyl 4-[6-(N-cyclopentylmethylcarbamoyl)-3-(2-methoxycarbonylethyl)indol-1-ylmethyl]-3-methoxybenzoate (1.04 g) in dioxane (6 ml) was treated with triethylamine (0.65 ml) and trimethylsilyl trifluoromethanesulphonate (0.8 ml). The solution was stirred for 24 hours and then was diluted with water to give a viscous oil. The liquids were decanted and the oil was triturated successively with water and hexane. The resultant solid was recrystallized from ethyl acetate/hexane to give 4-[6-(N-cyclopentylmethylcarbamoyl)-3-(2-methoxycarbonylethyl)indol-1-ylmethyl]-3-methoxybenzoic acid (0.3 g, 32%) as an ivory powder; mp 181–182°.

The starting bromoester of part (f) was prepared as follows:

(j) A solution of 3-methoxy-4-methylbenzoic acid (10.0 g), concentrated sulfuric acid (1 ml), and condensed isobutylene (200 ml) in methylene chloride (200 ml) was placed in a pressure vessel and stirred for 16 hours. The vessel was then opened to vent unreacted isobutylene. The remaining liquid was poured into 10% (w/v) sodium hydroxide solution (150 ml) and extracted twice with ethyl acetate. The combined extracts were washed with brine, dried ($MgSO_4$), and evaporated. The residue was purified by flash chromatography on silica gel (700 ml), eluting with 1:9 ethyl acetate:hexane, to give t-butyl 3-ethoxy-4methylbenzoate (9.1 g, 70%) as a colorless oil; NMR (80 MHz, $CDCl_3$) 1.6[s, 9H, $C(CH_3)_3$], 2.27(s, 3H, $CH_3$), 3.86(s, 3H, $OCH_3$), 7.11(d, 1H), 7.49(m, 2H).

A suspension of t-butyl 3-methoxy-4-methylbenzoate (8.9 g), N-bromosuccinimide (8.57 g), and benzoyl peroxide (0.1 g) in carbon tetrachloride (150 ml) was heated to reflux and irradiated with a sun lamp for 1 hour. After cooling to room temperature, the suspension was filtered; and the filtrate was evaporated. The residue was purified by flash chromatography on silica gel (700 ml), eluting with 5:95 ethyl acetate:hexane to give t-butyl 4-bromomethyl-3-methoxybenzoate (11.52 g, 95%) as a pale yellow oil; NMR (80 MHz, CDCl$_3$) 1.5[s, 9H, C(CH$_3$)$_3$], 3.9(s, 3H, OCH$_3$), 4.5(s, 2H, CH$_2$Br), 7.15(d, 1H), 7.4(m, 2H).

EXAMPLE 2

N-[4-[6-(N-Cyclopentylmethylcarbamoyl)-3-[2-(N-methylcarbamoyl)ethyl]indol-1-ylmethyl]-3-methoxybenzoyl]-2-methylbenzenesulphonamide A solution of 4-[6-(N-cyclopentylmethylcarbamoyl)-3-[2-(N-methylcarbamoyl)ethyl]indol-1-ylmethyl]-3-methoxybenzoic acid (0.25 g) (prepared as described in Example 1), 4-(dimethylamino)pyridine (0.07 g), 1-(3-dimethylaminopropyl)-3-ethylcarbodiimide hydrochloride (0.12 g), and ortho-toluenesulphonamide (0.09 g) in methylene chloride (3.0 ml) was stirred under a nitrogen atmosphere for 24 hours. The mixture was diluted with methylene chloride, washed sequentially with 10% (v/v) hydrochloric acid, water, and brine, and evaporated. The resulting ivory solid was purified by flash chromatography on silica gel (10 ml), eluting with 1:9 methanol:chloroform, to give the title compound (0.06 g, 17%) as an ivory powder; mp 211°–212°.

Analysis calculated for: C$_{35}$H$_{40}$N$_4$O$_6$S.0.1 H$_2$O: C, 65.02: H, 6.27; N, 8.66. Found: C, 64.73: H, 6.29; N, 8.66.

EXAMPLE 3 t-Butyl 4-[3-(2-cyanovinyl)-6-(N-cyclopentylmethylcarbamoyl)indol-1-ylmethyl]-3-methoxybenzoate Using a similar procedure to that described in Example 1, part (g), but using cyanomethylenetriphenylphosphorane in place of methyl (triphenylphosphoranylidene)acetate, the title compound was obtained as a yellow solid (78%); partial NMR (80 MHz, CDCl$_3$): 3.41(dd, 2H, CH$_2$N), 3.93(s, 2.1H, OCH$_3$, E-isomer), 3.97(s, 0.9H, OCH$_3$, Z-isomer), 5.20(d, 0.3H, CHCN, Z-isomer), 5.38(s, 1.4H, ArCH$_2$, E-isomer), 5.44(s, 0.6H, ArCH$_2$, Z-isomer), 5.74(d, 0.7H, CHCN, E-isomer), 6.19(broad, 1H, NH).

EXAMPLE 4

4-[3-(2-Cyanovinyl)-6-(N-cyclopentylmethylcarbamoyl)indol-1-ylmethyl]-3-methoxybenzoic acid Using a similar procedure to that described in Example 1, part (i), but starting from the compound of Example 3, the title compound was obtained as a white powder (87%); mp 277°–279°.

Analysis calculated for:
C$_{27}$H$_{27}$N$_3$O$_4$: C, 70.88; H, 5.95; N, 9.18. Found: C, 70.68; H, 6.02: N, 9.08.

EXAMPLE 5

N-[4-[3-(2-Cyanovinyl)-6-(N-cyclopentylmethylcarbamoyl)indol-1-ylmethyl]-3-methyoxybenzoyl]2-methylbenzenesulfonamide Using a similar procedure to that described in Example 2, but starting from the compound of Example 4, the title compound was obtained as a white solid (79%), mp 174–176° (d).

Analysis calculated for: C$_{34}$H$_{34}$N$_4$O$_5$S.0.5H$_2$O: C, 65.89; H, 5.69; N. 9.04. Found: C, 65.62: H, 5.63: N, 9.00.

EXAMPLE 6

N-[4-[6-(N-Cyclopentylmethylcarbamoyl)-3-[2-(morpholinocarbonyl)ethyl]indol-1-ylmethyl]-3-methyoxybenzoyl]benzenesulfonamide Using a similar procedure to the described in Example 2, but starting from 4-[6-(N-cyclopentylmethylcarbamoyl)-3-[2-(morpholinocarbonyl)ethyl]indol-1-ylmethyl]-3-methoxybenzoic acid and phenylsulfonamide, the title compound was obtained as a white solid (69%); mp 244°–245°.

Analysis calculated for: C$_{37}$H$_{42}$N$_4$O$_7$S: C, 64.70: H, 6.16; N, 8.16. Found: C, 64.65: H, 6.18: N, 7.96.

The starting indole was obtained as follows: A solution of 4-[6-(N-cyclopentylmethylcarbamoyl)-3-(2-methoxycarbonylethyl)indol-1-ylmethyl)]-3-methoxybenzoic acid (0.68g)(prepared as described in Example 1, parts (a) through (i)) and 4-(dimethylamino)pyridine (0.17 g) in morpholine (4 ml) was heated at 80° for 48 hours under a nitrogen atmosphere. The reaction was diluted with water and acidified with 10% (v/v) hydrochloric acid. The resultant precipitate was collected by filtration and washed with water. The product was purified by recrystallization from ethyl acetate to give 4-[6-(N-cyclopentylmethylcarbamoyl)-3-[2-(morpholinocarbonyl)ethyl]indol-1-ylmethyl]-3-methoxybenzoic acid as a white powder (0.31 g, 41%); partial NMR (80 MHz, CDCl$_3$) 1.2–1.8(m, 9H, cyclopentyl), 2.70(dd, 2H, CH$_2$NH), 3.15(t, 2H, COCH$_2$), 3.2–3.7(m, 8H, morpholino), 3.92(s, 3H, OCH$_3$), 5.35(s, 2H, ArCH$_2$), 6.58(t, 1H, NH), 7.17(d, 1H), 7.9(s, 1H, H$^7$-indole).

EXAMPLE 7

N-[4-[6-(N-Cyclopentylmethylcarbamoyl)-3-[2-(morpholinocarbonyl)ethyl]indol-1-ylmethyl]-3-methoxybenzoyl]-2-methylbenzenesulphonamide Using a similar procedure to the one described in Example 2, but starting from 4-[6-(N-cyclopentylmethylcarbamoyl)-3-[2-(morpholinocarbonyl)ethyl]indol-1-ylmethyl]-3-methoxybenzoic acid, prepared as described in Example 6, the title compound was obtained as a white powder (28%); mp 159°–161°.

Analysis calculated for: C$_{38}$H$_{44}$N$_4$SO$_7$: C, 65.12; H, 6.33; N, 7.99. Found: C, 64.75; H, 6.34: N, 7.88.

EXAMPLE 8

N-[4-[6-(N-Cyclopentylmethylcarbamoyl)-3-[2-(pyrrolidinocarbonyl)ethyl]indol-1-ylmethyl]-3-methoxybenzoyl]-2-methylbenzesulphonamide Using a similar procedure to the one described in Example 2, but starting from 4-[6-(N-cyclopentylmethylcarbamoyl)-3-[2-(pyrrolidinocarbonyl)ethyl]indol-1-ylmethyl]-3-methoxybenzoic acid, the title compound was obtained as a white powder (48%); mp 190°–191°.

Analysis calculated for: C$_{38}$H$_{44}$N$_4$SO$_6$: C, 66.64; H, 6.48; N, 8.18. Found: C, 66.44; H, 6.46; N, 8.02.

The starting indole was prepared as follows:

A solution of 4-[6-(N-cyclopentylmethylcarbamoyl)-3-(2-methoxycarbonylethyl)indol-1-ylmethyl]-3-methoxybenzoic acid (0.84 g) (prepared as described in Example 1, parts (a) through (i)) and 4-(dimethylamino)pyridine (0.21 g) in pyrrolidine (5 ml) was heated at 80° for 48 hours under a nitrogen atmosphere. The reaction was diluted with water and acidified with 10% (v/v) hydrochloric acid. The resultant precipitate was collected by filtration and washed with water to give 4-[6-(N-cyclopentylmethylcarbamoyl)-3-[2-(pyrrolidinocarbonyl)ethyl]indol-1-ylmethyl]-3-methoxybenzoic acid as a white powder (0.77 g, 85%): partial NMR (80 MHz, DMSO-$d_6$: 1.1–2.0 (m, 12H), 2.1(m, 1H, NHCH$_2$CH), 3.9(s, 3H, OCH$_3$), 6.7(d, 1H, Ar), 7.3(s, 1H, H$^2$-indole), 8.3(t,1H, NH).

EXAMPLE 9

N-[4-[6-(N-Cyclopentylmethylcarbamoyl)-3-[2-(N,N-dimethylcarbamoyl)propyl]indol-1-ylmethyl]-3-methoxybenzoyl]-2-methylbenzenesulphonamide.

Using a similiar procedure to that described in Example 2, but starting from 4-[6-(N-cyclopentylmethylcarbamoyl)-3-[2-(N,N-dimethylcarbamoyl)propyl]indol-1-ylmethyl]-3-methoxybenzoic acid, the title compound was obtained as a yellow powder (56%); mp 140°–143°.

Analysis calculated for: $C_{37}H_{44}N_4O_6S.0.5\ H_2O$: C, 65.18; H, 6.65; N, 8.21. Found: C, 65.15; H, 6.65: N, 8.11.

The starting material was prepared as follows:

(a) A solution of t-butyl 4-[6-(N-cyclopentylmethylcarbamoyl)-3-formylindol-1-ylmethyl]3-methoxybenzoate (Example 1, part(f)) (2.8 g) and (carbethoxyethylidene)triphenylphosphorane (4.6 g) in dioxane (29 ml) was heated at reflux for 18 hours. The solvent was evaporated. The resultant residue was purified by flash chromatography on silica gel (192 ml), eluting with 1:4 ethyl acetate:hexane to give t-butyl 4-[6-(N-cyclopentylmethylcarbamoyl)-3-(2-ethoxycarbonyl-1-propenyl)indol-1-ylmethyl]-3-methoxybenzoate (3.3 g, 100%) as a light yellow solid; mp 118°–120°; NMR (80 MHz, CDCl$_3$) 2.15(d, 3H, CCH$_3$), 3.40(dd, 2H, NHCH$_2$), 5.42(s, 2H, NCH$_2$), 6.22(br t, 1H, NH), 6.78(d, 1H, Ar).

(b) A solution of t-butyl 4-[6-(N-cyclopentylmethylcarbamoyl)-3-(2-ethoxycarbonyl-1-propenyl) indol-1-ylmethyl]-3-methoxybenzoate (3.3 g) in methanol (30 ml) was treated with 10% (w/w) palladium on carbon (0.8 g) and shaken under 3.45 bars of hydrogen for 18 hours. The catalyst was removed by filtration through diatomaceous earth, and the filtrate was evaporated to give t-butyl 4-[6-(N-cyclopentylmethylcarbamoyl)-3-(2-ethoxycarbonylpropyl)indol-1-ylmethyl]-3-methoxybenzoate (3.3 g, 100%) as a colorless oil: partial NMR (80 MHz, CDCl$_3$) 3.40(t, 2H, NHCH$_2$), 3.94(s, 3H, OCH$_3$), 4.10(q, 2H, OCH$_2$), 5.33(s, 2H, NCH$_2$), 6.14(br t, 1H, NH), 6.63(d, 1H, Ar), 7.04(s, 1H, H$^2$-indole), 7.85(br s, 1H, H$^7$indole).

(c) A solution of t-butyl 4-[6-(N-cyclopentylmethylcarbamoyl)-3-(2-ethoxycarbonylpropyl)indol-1-ylmethyl]-3-methoxybenzoate (0.75 g) in a mixture of tetrahydrofuran (3.5 ml), methanol (3.5 ml), and water (1.3 ml) was treated with lithium hydroxide monohydrate (0.33 g). The mixture was stirred at 30° for 6 hours and then concentrated to remove the organic solvents. The residue was dissolved in water, and the solution was acidified with 10% (v/v) hydrochloric acid. The precipitate which formed was collected by filtration and dried to give t-butyl 4-[6-(N-cyclopentylmethylcarbamoyl)-3-(2-carboxypropyl)indol-1-ylmethyl]-3-methoxybenzoate (0.68 g, 95%) as a white powder; mp 195°–197°; partial NMR (80 MHz, CDCl$_3$): 2.55–3.24(m, 3H, CH$_2$CHCH$_3$), 3.38(t, 2H, NHCH$_2$), 3.91(s, 3H, OCH$_3$), 5.24(s, 2H, NCH$_2$), 6.17(br t, 1H, NH), 6.61(d, 1H, Ar), 7.04(s, 1H, H$^2$-indole), 7.85(br s, 1H, H$^7$-indole).

(d) A solution of t-butyl 4-[6-(N-cyclopentylmethylcarbamoyl)-3-(2-carboxypropyl)indol1-ylmethyl]-3-methoxybenzoate (0.96 g) and 1,1'carbonyldiimidazole (0.42 g) in methylene chloride (9 ml) was heated at reflux under nitrogen for one hour. The solution was transferred under nitrogen to a pressure vessel containing condensed dimethylamine (60 ml). After the vessel was sealed, the mixture was heated at 60° for ninety hours. The amine was then allowed to evaporate. The residue was diluted with water, acidified with 50% (v/v) hydrochloric acid, and extracted with methylene chloride. The organic extract was washed with water and brine, dried (MgSO$_4$), and evaporated. The residue was purified by flash chromatography on silica gel (160 ml), eluting with 1:9 methanol:chloroform to give t-butyl 6-(N-cyclopentylmethylcarbamoyl)-3-[2-(N,N-dimethylcarbamoyl)pı opyl]indol-1-ylmethyl]-3-methoxybenzoate (0.53 g, 53%) as a white crystalline foam: mp 73°–75°: partial NMR (250 MHz: CDCl$_3$) 1.18(d, 3H, CHCH$_3$), 1.56(s, 9H, C(CH$_3$)$_3$), 2.07–2.28(m, 1H, CH$_3$CH), 2.75(s, 3H, NCH$_3$), 2.83(s, 3H NCH$_3$), 2.96–3.21(m, 2H, CH$_2$CHCH$_3$), 3.40 (dd, 2H, NHCH$_2$), 6.17(br t, 1H, NH), 6.60(d, 1H, Ar), 7.06(s, 1H, H$^2$-indole), 7.86(br s, 1H, H$^7$-indole).

(e) A solution of t-butyl 4-[6-(N-cyclopentylmethylcarbamoyl)-3-[2-(N,N-dimethylcarbamoyl)propyl]indol-1-ylmethyl]-3-methoxybenzoate (0.53 g) in dioxane (3 ml) was treated with triethylamine (0.31 ml) and trimethylsilyl trifluoromethanesulfonate (0.38 ml). The solution was heated under nitrogen at reflux for thirty minutes, allowed to cool, and then diluted with water to give a precipitate which was collected by filtration and dried under vacuum to give 4-[6-(N-cyclopentylmethylcarbamoyl)-3-[2-(N,N-dimethylcarbamoyl)propyl]indol-1-ylmethyl]-3-methoxybenzoic acid (0.33 g, 66%) as a yellow powder; mp 120°–122°; partial NMR (250 MHz, DMSO-$d_6$): 1.04(d, 3H, CHCH$_3$), 2.07–2.24(m, 1H, CH$_3$CH), 2.71(s, 3H, NCH$_3$), 2.80(s, 3H, NCH$_3$), 3.93(s, 3H, OCH$_3$), 5.42(s, 2H, NCH$_2$), 6.58(d, 1H, Ar), 7.30(s, 1H, H$^2$-indole), 7.40(d, 1H, H$^5$-indole), 7.90(br s, 1H, H$^7$-indole), 8.33(br t, 1H, NH).

EXAMPLE 10

4-[6-(N-Cyclopentylmethylcarbamoyl)-3-(dimethylcarbamoyloxymethyl)indazol-1-ylmethyl]-3-methoxybenzoic acid Using a similar ester hydrolysis to the procedure described in Example 9, part (c), but starting from methyl 4-[6-(N-cyclopentylmethylcarbamoyl)-3-(dimethylcarbamoyloxymethyl)indazol-1-ylmethyl]-3-methoxybenzoate, the title compound may be obtained as a solid.

The starting indazole was made as follows:

(a) To a solution of boron trifluoride etherate (18 ml) in chloroform (450 ml, Al$_2$O$_3$ treated) at −15° was added a solution of 3-amino-4-methylbenzoic acid (15.1 g) in tetrahydrofuran (150 ml) over 15 minutes and the resulting mixture was then stirred for an additional 5 minutes. To this mixture was added t-butyl nitrite (14 ml), and the reaction was warmed to 5°. After stirring for 1 hour, potassium acetate (49 g) and 18-crown-6 (2.65 g) were added. The reaction mixture was allowed to warm to room temperature and stirred for 72 hours. The reaction mixture was evaporated, and 3:7 acetone:ethyl acetate (500 ml) and 1N hydrochloric acid (150 ml) were added. After stirring for 2 hours, brine (150 ml) was added to the mixture and the mixture filtered. The aqueous filtrate was extracted with 3:7 acetone:ethyl acetate (2×100 ml). The combined organic extract was dried (MgSO$_4$) and evaporated. The resulting residue was dissolved in hot acetic acid (250 ml) and 250 ml saturated ethereal HCl and 250 ml ether were added sequentially. After cooling to room temperature, the precipitate was filtered and treated with 3:7 acetone-:ethyl acetate (500 ml) and brine (100 ml) for 1 hour. After the phases were separated, the aqueous layer was extracted with ethyl acetate (100 ml). The combined organic extracts were washed with brine, dried (MgSO₄) and evaporated to afford 6-carboxyindazole as a brown solid (9.8 g, 57%), mp >250°.

(b) To a solution of 6-carboxyindazole (4.0 g) in acetic acid (140 ml) was added bromine (1.53 ml), and the mixture was stirred in the dark for 24 hours. After the addition of saturated sodium bisulfite (50 ml) and brine (100 ml), the mixture was extracted with ethyl acetate. The organic layer was washed with brine, dried (MgSO₄) and evaporated. The resulting solid was powdered and vacuum dried to afford 3-bromo-6-carboxyindazole as a light brown solid (5.88 g, 99%), mp >250°.

(c) To a mixture of 3-bromo-6-carboxyindazole (5.84 g), cyclopentylmethylamine (3.48 ml), 1-(3-dimethylaminopropyl)-3-ethylcarbodiimide hydrochloride (3.25 g), methylene chloride (120 ml) and dimethylformamide (40 ml) was added 4-dimethylaminopyridine (5.10 g). After stirring for 48 hours, the reaction mixture was added to 450 ml ethyl acetate; washed with 1N hydrochloric acid, 0.5M sodium carbonate and brine: dried (MgSO₄); and evaporated. The residue was flash chromatographed over 175 g silica gel, eluting sequentially with methylene chloride (350 ml), 15:85 ethyl acetate:methylene chloride (350 ml), and 1:3 ethyl acetate:methylene chloride to afford 3-bromo-6-(N-cyclopentylmethylcarbamoyl)indazole as a light red solid (5.6 g, 72%), mp 119°–125°.

(d) A mixture of 60% sodium hydride dispersion (13 mg) was washed with petroleum ether, and dimethylformamide (0.75 ml) was added. This mixture was cooled to 0° and a solution of 3-bromo-6-(N-cyclopentylmethylcarbamoyl)indazole (107 mg) in dimethylformamide (0.75 ml) was added. After stirring for 30 minutes, methyl 4-bromomethyl-3-methoxy benzoate (95 mg) was added. After 15 minutes of stirring at 0°, the mixture was allowed to warm to room temperature. The reaction was stirred for 1.5 hours and ethyl acetate (40 ml) was added. The solution was washed with brine, water and brine; dried (MgSO₄) and evaporated. The residue was flash chromatographed over 10 g of silica gel, eluting with 5:95 ethyl acetate:methylene chloride to afford methyl 4-[3-bromo-6-(N-cyclopentylmethylcarbamoyl)indazol-1-ylmethyl]-3-methoxybenzoate as a white solid (136 mg, 82%), mp 161.0°–162.5°;

Analysis calculated for: C₂₄H₂₇BrN₃O₄: C, 57.49; H, 5.42; N, 8.38. Found: C, 57.53; H, 5.29; N, 8.28.

(e) To a solution of zinc bromide (6.75 g) (dried at 180° at 67 Pa for 2 hours) in tetrahydrofuran (90 ml) at 0° was added 1M vinylmagnesium bromide (25 ml) in ether. The reaction was allowed to stir at room temperature for 15 minutes before dichloro[1,1'bis(diphenylphosphino)ferrocene]palladium (II) (183 mg) was added to the reaction, and the reaction was heated at 45° for 120 hours. Additional portions of the palladium reagent (each 183 mg) were added after 48 and 84 hours of stirring. The reaction mixture was cooled to 0°, and 1N hydrochloric acid (50 ml) and ethyl acetate (250 ml) were added. The mixture was stirred for 15 minutes before it was filtered through diatomaceous earth with ethyl acetate washings. The organic layer was washed with water and brine, dried (MgSO₄), and evaporated. Flash chromatography of the residue over 200 g silica gel, eluting with methylene chloride (800 ml), 2.5:97.5 ethyl acetate:methylene chloride (500 ml), and 5:95 ethyl acetate:methylene chloride afforded a solid. Recrystallization from methylene chloride and petroleum ether yielded methyl 4-[6-(N-cyclopentylmethylcarbamoyl)-3-vinylindazol-1-ylmethyl]-3-methoxybenzoate as a colorless solid (944 mg, 42%), mp 138°–140°, resolidifies and remelts at 168.0°–170.0° mass spectrum (chemical ionization) 448 (M+H).

(f) A solution of methyl 4-[6-N-cyclopentylmethylcarbamoyl)-3-vinylindazol-1-ylmethyl]3-methoxybenzoate (700 mg) in 1:1 methylene chloride: methanol (30 ml) at −78° was ozonized for 25 minutes. Excess ozone was removed by passing oxygen through the reaction for 5 minutes. Sodium borohydride (100 mg) was added and the mixture allowed to warm to room temperature. After stirring for 2 hours, the mixture was cooled to 0°, quenched with 1N hydrochloric acid, and extracted with ethyl acetate (100 ml). The organic layer was washed with 1N hydrochloric acid, brine and water. The organic layer containing insoluble precipitate was concentrated to about 50 ml and filtered. The solid was powdered and vacuum dried over potassium hydroxide for 18 hours to afford methyl 4-[6-(N-cyclopentylmethylcarbamoyl)-3-hydroxymethylindazol-1-ylmethyl]-3-methoxybenzoate as a colorless solid (569 mg, 81%), mp 187.0°–187.5°; mass spectrum (chemical ionization) 452 (M+H).

(g) To a suspension of 60% sodium hydride dispersion (13 mg) (petroleum ether washed) in tetrahydrofuran (1 ml) at 0° was added a solution of methyl 4-[6-(N-cyclopentylmethylcarbamoyl)-3-hydroxymethylindazol-1-ylmethyl]-3-methoxybenzoate (151 mg) in 7:1 dimethylformamide:tetrahydrofuran (8 ml). After stirring for 45 minutes, dimethylcarbamoyl chloride (0.033 ml) was added. The reaction was stirred for 15 minutes and was allowed to warm to room temperature. After 3 hours, 1N hydrochloric acid was added and the mixture was extracted with ethyl acetate. The organic layer was washed with brine and dried (MgSO₄). Evaporation and flash chromatography over 15 g silica gel, eluting with 2:8 ethyl acetate:methylene chloride (50 ml) and 4:6 ethyl acetate:methylene chloride, afforded methyl 4-[6-(N-cyclopentylmethylcarbamoyl)-3-(dimehylcarbamoyloxymethyl)indazol-1-ylmethyl]-3-methoxybenzoate as a colorless solid (40 mg, 23%); mass spectrum (chemical ionization) 523 (M+H). NOTE: Still further Examples of compounds of the invention are provided by the benzoic acid starting materials for formula I (M=CO₂H) described in connection with Examples 6, 8 and 9.

EXAMPLE 11

The following illustrates representative pharmaceutical dosages forms which may be used for the therapeutic or prophylactic administration of an acidic compound of formula I (that is, M is an acidic group as defined herein before) or of a pharmaceutically acceptable salt thereof (hereinafter referred to as 'Compound X'):

| (i) | Tablet 1 | mg/tablet |
|---|---|---|
| | 'Compound X' | 100 |
| | Lactose | 182.75 |
| | Croscarmellose Sodium | 12.0 |

-continued

| | | |
|---|---|---|
| | Starch | 2.25 |
| | Magnesium stearate | 3.0 |
| (ii) | Tablet 2 | mg/tablet |
| | 'Compound X' | 20 |
| | Microcrystalline cellulose | 420 |
| | Polyvinylpyrrolidone | 14.0 |
| | Starch | 43.0 |
| | Magnesium stearate | 3.0 |
| (iii) | Capsule | mg/capsule |
| | 'Compound X' | 10 |
| | Lactose | 488.5 |
| | Magnesium stearate | 1.5 |
| (iv) | Injection 1 | (10 mg/ml) |
| | 'Compound X' (free acid form) | 1.0% w/v |
| | Sodium phosphate | 3.6% w/v |
| | 0.1M Sodium hydroxide solution | 15.0% w/v |
| | Water for 'to 100% | |
| (v) | Injection 2 (buffered to pH 6) | (1 mg/ml) |
| | 'Compound X' (free acid form) | 0.1% w/v |
| | Sodium phosphate | 2.26% w/v |
| | Citric acid | 0.38% w/v |
| | Polyethylene glycol 400 | 3.5% w/v |
| | Water for injection to 100% | |
| (vi) | Aerosol | mg/ml |
| | 'Compound X' | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |

It will be appreciated that the above pharmaceutical compositions may be varied according to well known pharmaceutical techniques to accommodate differing amounts and types of active ingredient 'Compound X'. The aerosol (vi) may be used in conjunction with a standard, metered dose aerosol dispenser.

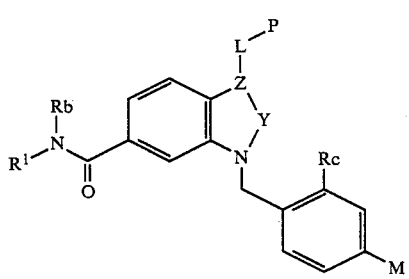

I

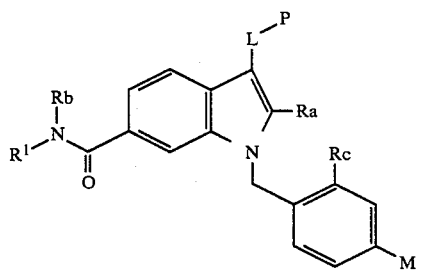

Ia

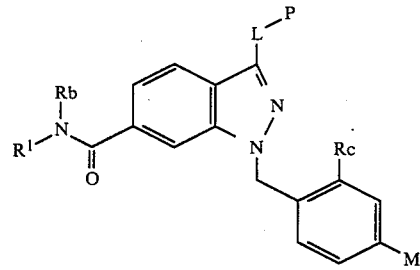

Ib

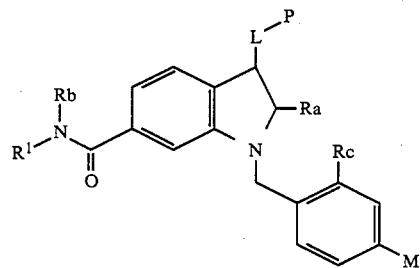

Ic

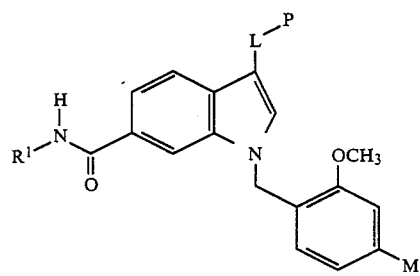

IIa

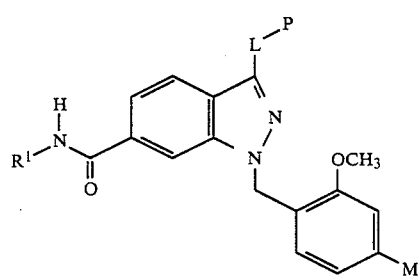

IIb

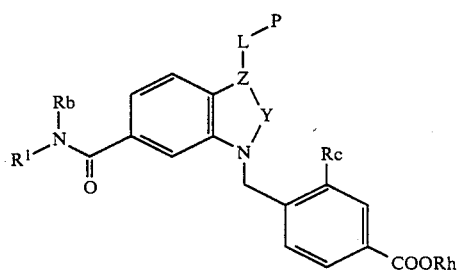

III

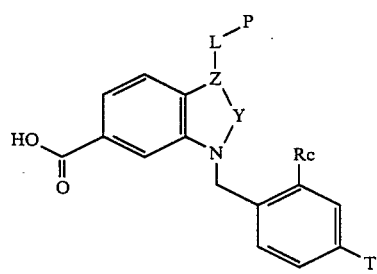

IV

-continued

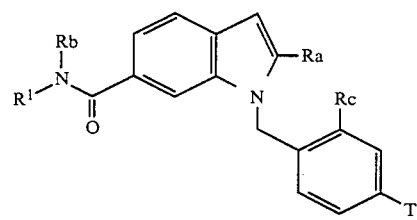

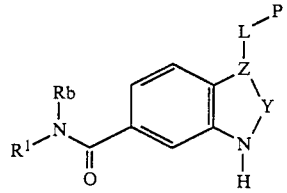

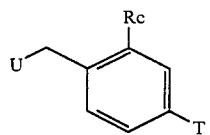

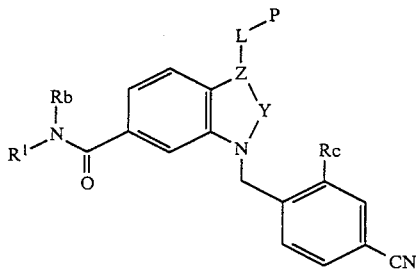

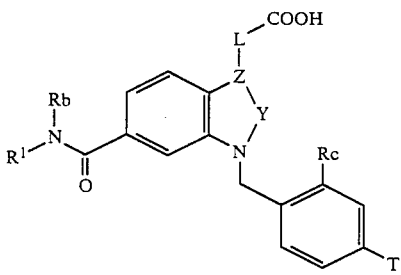

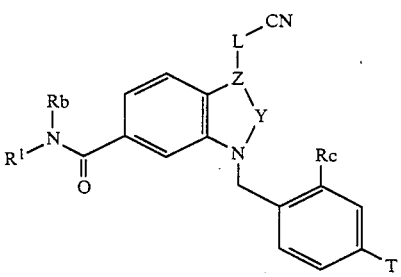

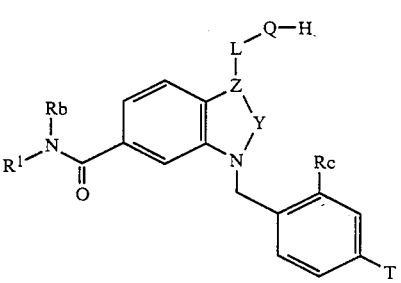

-continued

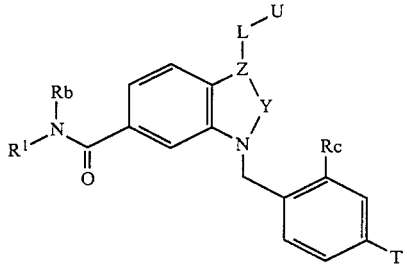

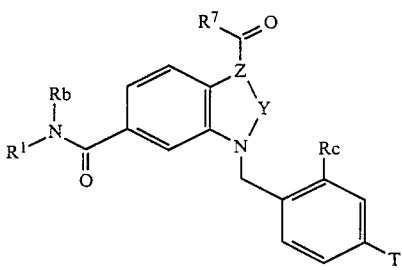

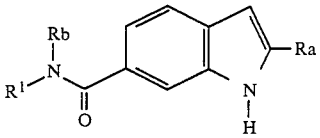

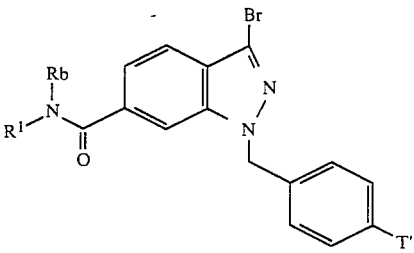

What is claimed is:
1. A compound of formula Ia

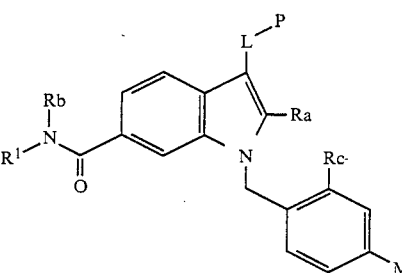

wherein
Ra is hydrogen or (1–4C)alkyl;
Rb is hydrogen or methyl;
$R^1$ is (2–10C)alkyl which may contain 1 or more fluorine substituents; or $R^1$ is phenyl-(1–6C)alkyl in which the (1–6C)alkyl moiety may bear a fluoro or (1–4C)alkoxy substituent and in which the phenyl moiety may bear a substituent selected from a group consisting of halogeno, (1–4C)alkyl, (1–4C)alkoxy and trifluoromethyl; or $R^1$ is (3–8C)cycloalkyl or (3–8C)cycloalkyl-(1–6C)alkyl, the cyclic moiety of any of which may contain one unstruated linkage and may bear 1 or 2 (1-4C)alkyl substituents;

L is a (1-10C)alkylene link, which may contain one double or triple bond;

P is a polar group selected from a group consisting of cyano, 1H-tetrazol-5-yl, carbamoyl of formula $CONR^2R^3$, ureido of formula $NR^4CONR^2R^3$, carbamoyloxy of formula $OCONR^2R^3$, a carbamate of formula $NR^4COOR^5$, acylamino of formula $NR^4COR^5$, acyloxy of a formula $OCOR^5$, and a thio group (which may be oxidized) of formula $S(O)_nR^5$ in which $R^2$ is selected from a group consisting of hydrogen, (1-6C)alkyl, and phenyl, the phenyl moiety of which may bear 1 or 2 substituents selected from a group consisting of halogeno, (1-4C)alkyl, (1-4C)alkoxy and trifluoromethyl, and $R^3$ and $R^4$ are independently selected from a group consisting of hydrogen and (1-6C)alkyl;

or $R^2$ and $R^3$ together with the adjacent nitrogen form a pyrrole, pyrrolidine, piperidine, morpholine, piperazine or N-(1-6C)alkylpiperazine ring, and $R^4$ is hydrogen or (1-6C)alkyl;

$R^5$ is chosen from a group consisting of (1-4C)alkyl and phenyl, the phenyl moiety of which may bear 1 or 2 substituents selected form a group consisting of halogeno, (1-4C)alkyl, (1-4C)alkoxy and trifluoromethyl; and n is the integer 0, 1 or 2;

Rc is selected from a group consisting of hydrogen and (1-4C)alkoxy; and

M is an acidic group selected from a group consisting of carboxy, an acylsulphonamide residue of formula $-CO.NH.SO_2R^6$ and 1H-tetrazol-5-yl in which $R^6$ is selected from a group consisting of (1-6C)alkyl, (3-8C)cycloalkyl, (6-12C)aryl, heteroaryl selected from a group consisting of furyl, thienyl and pyridyl, and (6-12C)aryl(1-4C)alkyl, in which any of the aromatic or heteroaromatic moieties may bear 1 or 2 substituents selected from a group consisting of halogeno, (1-4C)alkyl, (1-4C)alkoxy, and trifluoromethyl;

or a pharmaceutically acceptable salt thereof.

2. A compound as claimed is claim 1 having the formula IIa

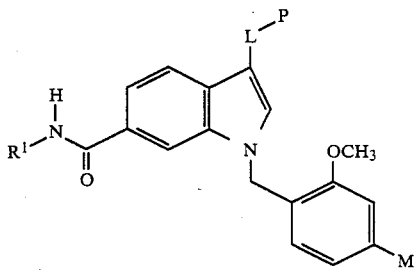

IIa wherein $R^1$, L, M, and P have any of the meanings defined in claim 1.

3. A compound as claimed in claim 1 wherein

Ra is hydrogen;

Rb is hydrogen or methyl;

$R^1$ is (3-7C)alkyl which may contain 1 or more fluorine substituents; or $R^1$ is phenyl-(1-4C)alkyl in which the (1-4C)alkyl moiety may bear a fluoro or (1-4C)alkoxy substituent and in which the phenyl moiety may bear a subtituent selected from a group consisting of halogeno, (1-4C)alkyl, (1-4C)alkoxy and trifluoromethyl; or $R^1$ is (3-6C)cycloalkyl or (3-6C)cycloalkyl-(1-4C)alkyl, the cyclic moiety of which may contain one unsaturated linkage and may bear 1 or 2 (1-4C)alkyl substituents;

L is a (1-5C)alkylene link, which may contain one double or triple bond;

P is a polar group selected from a group consisting of cyano, 1H-tetrazol-5-yl, carbamoyl of formula $CONR^2R^3$, carbamoyloxy of formula $OCONR^2R^3$, and a thio group (which may be oxidized) of formula $S(O)_nR^5$ in which $R^2$ is selected from a group consisting of hydrogen, (1-6C)alkyl, and phenyl, the phenyl moiety of which may bear 1 or 2 substituents selected from a group consisting of halogeno, (1-4C)alkyl, (1-4C)alkoxy and trifluoromethyl, and $R^3$ is hydrogen or (1-6C)alkyl; or $R^2$ and $R^3$ together with the adjacent nitrogen form a pyrrole, pyrrolidine piperidine, morpholine, piperazine or N-(1-6C)alkylpiperazine ring;

$R^5$ is chosen from a group consisting of (-4C)alkyl and phenyl, the phenyl moiety of which may bear 1 or 2 substituents selected from a group consisting of halogeno, (1-4C)alkyl, (1-4C)alkoxy and trifluoromethyl; and n is the integer 1 or 2;

Rc is selected from a group consisting of hydrogen and (1-4C)alkoxy; and

M is an acidic group selected from a group consisting of carboxy, an acysulphonamide residue of formula $-CO.NH.SO_2R^6$ and 1H-tetrazol-5-yl in which $R^6$ is selected from a group consisting of (1-4C)alkyl, (3-6C)cycloalkyl, (6-12C)aryl, heteroaryl selected from a group consisting of furyl, thienyl and pyridyl, and (6-12C)aryl-(1-4C)alkyl, in which any of the aromatic or heteroaromatic moieties may bear 1 or 2 substituents selected from a group consisting of halogeno, (1-4C)alkyl, (1-4C)alkoxy, and trifluoromethyl.

4. A compound as claimed in claim 1 wherein

Ra is selected from a group consisting of hydrogen, methyl, ethyl, propyl and isopropyl;

Rb is hydrogen; $R^1$ is selected from a group consisting of (a) ethyl, propyl, isopropyl, butyl, isobutyl, sec-butyl, t-butyl, pentyl, 3-methylbutyl, 1-ethylpropyl, hexyl, heptyl, 1-ethylpentyl or nonyl, of which may contain 1 or more flourine substituents; (b) benzyl, 1-phenylethyl, 2-phenylpropyl, 3-phenylpropyl, 1-methyl-1-phenylethyl, 1-phenylbutyl and 1-phenylpentyl, each of which may be substituted on the alkyl moiety by methoxy or ethoxy and each of which may be substituted on the phenyl moiety by a member selected from a group consisting of fluoro, chloro, bromo, methyl, ethyl, methoxy and ethoxy; (c) cyclopropyl, cyclobutyl, cyclopentyl, cyclohexyl, cycloheptyl, cyclobutylmethyl, cyclopentylmethyl, cyclohexylmethyl, 1-cyclopentylethyl, 2-cyclopentylethyl, 1-cyclopentylpropyl, 1-cyclohexylpropyl, 1-cyclopentylbutyl and 1-cyclohexylbutyl, wherein each of the cyclic moieties may be substituted by methyl, ethyl, or isopropyl; and (d) cyclopentenyl, cyclohexenyl, cyclopentenylmethyl, 1-cyclohexen-4-ylmethyl, and 1-(cyclohexenyl)butyl wherein each of the cyclic moieties may be substituted by methyl, ethyl or isopropyl;

L is selected from a group consisting of (a) methylene, ethylene, ethylidene, trimethylene, tetramethylene, 1,1-demethylethylene, 2,2-dimethylethylene, pentamethylene, and hexamethylene; (b) vinylene, 1-propenylene, 2-propenylene, 2-methyvinylene, 1-butenylene, 2-butenylene, 1,2-dimethylvinylene, 1,1-dimethyl-2-propenylene and 3,3-dimethyl-1-propenylene; and (c) ethynylene, 1-propynylene, 2-propynylene, 2-butynylene, 1,1-dimethyl-2-propynylene and 3,3-dimethyl-1-propynylene;

$R^2$ is selected from a group consisting of hydrogen, methyl, ethyl, propyl, isipropylm butyl, t-butyl, pentyl, the phenyl moiety of which may bear 1 or 2 substituents selected form a group consisting of fluoro, chloro, bromo, methyl, ethyl, methoxy, ethoxy, and trifluoromethyl; and $R^3$ and $R^4$ are independently selected from a group consisting of hydrogen methyl, ethyl, propyl, isopropyl, butyl, t-butyl and pentyl; or $R^2$ and $R^3$ together with the adjacent nitrogen form a pyrrole, pyrrolidine, piperidine, piperazine, or N-alkyl piperazine ring in which N-alkyl group is selected from a group consisting of methyl, ethyl, propyl, isopropyl; butyl, t-butyl and pentyl, and $R^4$ is selected from a group consisting of hydrogen, methyl, ethyl, propyl, isopropyl, butyl, t-butyl and pentyl; and $R^5$ is selected from a group consisting of methyl, ethyl, propyl, isopropyl and phenyl, the phenyl group of which may bear 1 or 2 substituents independently selected from the group defined above for a phenyl group of R2;

Rc is methoxy or ethoxy; and $R^6$ is methyl, ethyl, propyl, isopropyl, butyl, cyclopentyl, cyclohexyl, phenyl, 1-naphthyl, 2-naphthyl, furyl, thienyl, pyridyl, benzyl, 1-naphthylmethyl or 2-naphthylmethyl wherein each aromatic or heteroaromatic moiety may be substituted as defined above for phenyl moiety in R2.

5. A compound as claimed in claim 1 wherein $R^1$ is thenyl, propyl, isopropyl, butyl, isobutyl, sec-butyl, t-butyl, pentyl, 3-methylbutyl, 1-ethylpropyl, hexyl, heptyl, 1-ethylpentyl, nonyl, benzyl, 4-chlorobenzyl, 4-trifluoromethylbenzyl, 4-methylbenzyl, 1-phenylethyl, 2-phenylethyl, 1-methyl-1-phenylethyl, 1-phenylpropyl, 1-phenylpentyl, cyclopentyl, cyclohexyl, cyclobutylmethyl, cyclopentylmethyl, cyclohexylmethyl, 2-cyclopentylethyl, 1-cyclopentylbutyl, 1-cyclohexylpropyl, 1-cyclohexylbutyl, cyclopentenylmethyl, and 1-cyclohexen-4-yl-methyl;

$R^2$, $R^3$ and $R^4$ are selected from a group consisting of (a) $R^2$ is hydrogen, methyl, ethyl, propyl, isopropyl, t-butyl, phenyl 2-methylphenyl or 4-chlorophenyl and $R^3$ and $R^4$ are independently selected to be hydrogen, methyl, or ethyl; and (b) $R^2$ and $R^3$ together with the adjacent nitrogen form a piperidine, morpholine, or N-methylpiperazine ring and $R^4$ is hydrogen, methyl or ethyl;

$R^5$ is methyl, ethyl, propyl, isopropyl, phenyl, 2-methylphenyl or 4-chlorophenyl;

$R^6$ is methyl, isopropyl, butyl, cyclopentyl, phenyl, 4-chlorophenyl, 4-methylphenyl, 2-chlorophenyl, 2-methylphenyl, 2-methoxyphenyl, naphthyl, thien-2-yl or 6-chloropyrid-3-yl;

Ra is hydrogen or methyl;

Rb is hydrogen; and

Rc is hydrogen or methoxy.

6. A compound as claimed in claim 5 wherein $R^1$ is butyl, 3-methylbutyl, 1-ethylpentyl, 1-phenylpropyl, cyclopentyl, or cyclopentylmethyl; $R^6$ is phenyl or 2-methylphenyl; Ra is hydrogen; and Rc is methoxy.

7. A compound as claimed in claim 1, 3, 2, 4, 5 or 6 wherein M is a radical of formula $-CO.NH.SO_2R^6$ wherein $R^6$ is phenyl; which may be substituted as defined in claim 1.

8. A compound as claimed is claim 7 wherein $R^1$ is cyclopentylmethyl; Ra and Rb are hydrogen; Rc is methoxy: L is methylene, ethylene, 2-methylethylene or vinylene; M is carboxy or an acylsulphonamide residue of formula $-CO.NH.SO_2R^6$ in which $R^6$ is phenyl or 2-methylphenyl; and P is cyano, carbamoyl of formula $CONR^2R^3$ or carbamoyloxy of formula $OCONR^2R^3$ wherein $R^2$ and $R^3$ are independently hydrogen or methyl, or $R^2$ and $R^3$ together with the adjacent nitrogen form a pyrrolidine or morpholine ring.

9. A compound as claimed in claim 1 selected form a group consisting of N-[4-[6-(N-cyclopentylemthylcarbamoyl)3-[2(morpholinocarbonyl)-ethyl]indol-1-ylemthyl]-3-methoxybenzoyl]2-methylbenzenesulphonamide and N-[4-[6-(N-cyclopentyllmethylcarbamoyl)-3-[2-(pyrrolidinocarbonyl)ethyl]indol-1-ylmethyl]-3-methoxybenzoyl]-2-methylbenzesulphomamide or a pharmaceutically acceptable salt thereof.

10. A salt as claimed in claim 1 wherein said salt is made with a base forming a physiologically acceptable cation.

11. A pharmaceutical composition comprising a leukotriene antagonizing amount of a compound of claim 1 or a pharmaceutically acceptable salt thereof and a pharmaceutically acceptable diluent or carrier.

12. A method of antagonizing the action of at least one type of leukotriene in a mammal requiring such treatment comprising administering to said mammal an effective amount of a compound of claim 1.

13. A method for the treatment of a selected allergic or inflammatory disorder in a mammal in need of such treatment comprising administering an effective amount of a compound of claim 1 to such mammal.

14. A composition as claimed in claim 11 wherein said composition is in the form of a liquid or powdered aerosol.

* * * * *

UNITED STATES PATENT AND TRADEMARK OFFICE
CERTIFICATE OF CORRECTION

PATENT NO. : 4,898,863

DATED : FEBRUARY 6, 1990

INVENTOR(S) : BROWN ET AL.

It is certified that error appears in the above-identified patent and that said Letters Patent is hereby corrected as shown below:

Column 30, line 22, "(-4C)alkyl" should read --(1-4C)alkyl--.

Column 31, line 33, "R2" should read --$R^2$--.

Column 31, line 42, "$R^1$ is thenyl, " should read --$R^1$ is ethyl,--

Column 32, line 34, "1-ylem-" should read --1-ylme- --.

Column 32, line 35, "methoxybenzoyl]2-" should read --methoxybenzoyl]-2- --.

Column 32, line 36, "N-[4-[6-(N-cyclopentyllmethylcarbamoyl)-3-" should read --N-[4-[6-(N-cyclopentylmethylcarbamoyl)-3---.

Signed and Sealed this

Twenty-third Day of February, 1993

*Attest:*

STEPHEN G. KUNIN

*Attesting Officer*      Acting Commissioner of Patents and Trademarks